United States Patent [19]
von der Saal et al.

[11] Patent Number: 4,831,032

[45] Date of Patent: May 16, 1989

[54] CARDIOTONIC BENZIMIDAZOLES

[75] Inventors: Wolfgang von der Saal, Weinheim; Alfred Mertens, Schriesheim; Herbert Berger, Mannheim; Bernd Muller-Beckmann, Grunstadt; Klaus Strein, Hemsbach, all of Fed. Rep. of Germany

[73] Assignee: Boehringer Mannheim GmbH, Mannheim, Fed. Rep. of Germany

[21] Appl. No.: 881,983

[22] Filed: Jul. 3, 1986

[30] Foreign Application Priority Data

Jul. 5, 1985 [DE] Fed. Rep. of Germany ....... 3524067

[51] Int. Cl.$^4$ ................... A61K 31/50; C07D 487/04; C07D 498/04
[52] U.S. Cl. .................................. 514/254; 514/183; 514/212; 514/226.8; 514/227.2; 514/228.5; 514/228.8; 514/232.8; 514/241; 514/245; 514/253; 514/256; 514/322; 514/338; 514/359; 514/361; 514/362; 514/363; 514/364; 514/365; 514/366; 514/369; 514/370; 514/372; 514/374; 514/375; 514/376; 514/377; 514/378; 514/380; 514/381; 514/382; 514/383; 514/384; 514/387; 514/388; 514/394; 514/395; 540/603; 544/54; 544/55; 544/58.5; 544/58.7; 544/96; 544/98; 544/135; 544/137; 544/139; 544/179; 544/180; 544/212; 544/238; 544/319; 544/328; 544/333; 544/405; 546/199; 546/271; 548/127; 548/128; 548/129; 548/130; 548/131; 548/132; 548/133; 548/134; 548/135; 548/137; 548/138; 548/141; 548/142; 548/143; 548/144; 548/151; 548/181; 548/213; 548/214; 548/218; 548/225; 548/233; 548/235; 548/236; 548/243; 548/245; 548/247; 548/248; 548/251; 548/254; 548/255; 548/263; 548/264; 548/266; 548/267; 548/269; 548/305; 548/306; 548/326

[58] Field of Search .............. 548/151, 218, 305, 306, 548/326, 127–135, 137, 138, 141–144, 181, 213, 214, 225, 233, 235, 236, 243, 245, 247, 248, 251, 254, 255, 263, 264, 266, 267, 269; 514/366, 375, 394, 395, 183, 212, 226.8, 227.2, 228.5, 228.8, 232.8, 241, 245, 253, 254, 256, 322, 338, 359, 361–365, 369, 370, 372, 374, 376–378, 380–384, 387, 388; 544/55, 58.5, 58.7, 96, 98, 135, 137, 139, 179, 180, 212, 238, 319, 328, 333, 405; 546/199, 271; 540/603

[56] References Cited

PUBLICATIONS

Chem. Abst., 71, 4077u (1969).
Chem. Abst., 68, 78263m (1968).
Chem. Abst., 90, 105583d (1979).

Primary Examiner—Richard A. Schwartz
Attorney, Agent, or Firm—Felfe & Lynch

[57] ABSTRACT

The present invention provides benzimidazoles of the general formula:

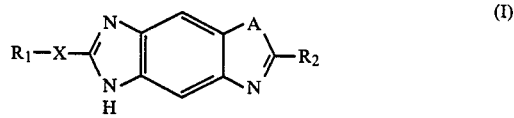

wherein $R_1$, X, A, and $R_2$ are as defined in the specification.

The present invention also provides processes for the preparation of these new benzimidazoles and pharmaceutical compositions containing them, as well as intermediates for the preparation thereof.

The new benzimidazoles are useful to treat heart or circulatory diseases which respond to a lowering of blood pressure, a positive inotropic action and/or an improvement in microcirculation.

20 Claims, No Drawings

CARDIOTONIC BENZIMIDAZOLES

The present invention is concerned with new benzimidazoles, processes for the preparation thereof and pharmaceutical compositions containing them.

The new benzimidazoles according to the present invention are compounds of the general formula:

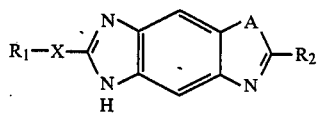

wherein $R_1$ is a heterocyclic five-membered ring containing up to 4 heteroatoms or a heterocyclic six-membered ring containing up to 5 heteroatoms, the heteroatoms in the said five- and six-membered rings being the same or different and being nitrogen, oxygen or sulphur atoms, one or more of said nitrogen atoms optionally carrying an oxygen atom, said five- and six-membered rings being optionally substituted one or more times by alkyl, alkoxy, alkylthio, hydroxyl, nitro, amino, halogen or cyano, or $R_1$ is a phenyl radical of the general formula:

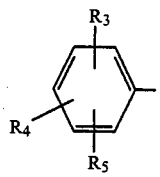

wherein $R_3$, $R_4$ and $R_5$, which can be the same or different, are hydrogen atoms or alkanesulphonyloxy, trifluoromethanesulphonyloxy, alkanesulphonylamino, trifluoromethanesulphonylamino, N-alkyl-alkanesulphonylamino, N-alkyl-trifluoromethanesulphonylamino, alkylsulphenylmethyl, alkylsulphinylmethyl or alkylsulphonylmethyl radicals, or are carbonyl groups substituted by a hydroxyl, alkoxy, amino, hydrazino, alkylamino, dialkylamino or cyclic imino group, whereby a methylene group can be replaced by a sulphur or oxygen atom, or are sulphonyl groups substituted by an amino, alkylamino, dialkylamino or cyclic imino group, whereby a methylene group can be replaced by a sulphur or oxygen atom, or are alkylcarbonylamino, N-alkyl-alkylcarbonylamino, aminocarbonylamino, alkylaminocarbonylamino or dialkylaminocarbonylamino radicals or are alkylthio, alkylsulphinyl, alkylsulphonyl or alkyloxysulphonyl radicals, or are alkenyloxy, alkynyloxy, cyanoalkoxy, carboxyalkoxy, alkoxycarbonylalkoxy radicals or are nitro, halogen, amino, mercapto, hydroxyl, alkyl, alkoxy, dialkylamino, 1-imidazolyl, trifluoromethyl or cyano groups or, when X represents a valency bond, besides the above-mentioned groups, $R_1$ can also be an alkyl, alkenyl, alkynyl, cycloalkyl, cycloalkenyl, halogenalkyl, trifluoromethyl, hydroxyl, mercapto, amino, alkylthio, pyridylcarbonylamino, carboxyalkyl, alkoxycarbonylalkyl or alkoxyalkyl group; X is a valency bond, a $C_1$-$C_4$-alkylene radical or a vinylene radical, A is an oxygen or sulphur atom or an

group, wherein $R_6$ is a hydrogen atom or an alkyl radical and $R_2$ is a hydrogen atom, a hydroxyl, mercapto or amino group or an alkyl, alkylthio, alkylcarbonylamino, N-alkyl-alkylcarbonylamino, alkylaminocarbonylamino, dialkylaminocarbonylamino, aminocarbonylamino or pyridylcarbonylamino group; as well as the tautomers thereof and the physiologically acceptable salts thereof with inorganic and organic acids.

When compounds of general formula (I) contain an asymmetric atom, the present invention also includes the optically-active forms and the racemic mixtures of these compounds.

The new compounds according to the present invention have valuable pharmacological properties and, in particular, they increase the power of the heart and/or have a blood pressure-lowering action and/or influence the thrombocyte function and improve the microcirculation.

When $R_1$ signifies a heterocyclic five-membered ring with up to 4 heteroatoms or a heterocyclic six-membered ring with up to 5 heteroatoms, wherein the heteroatoms in the said five- and six-membered rings can be the same or different and signify nitrogen, oxygen or sulphur atoms and optionally carry an oxygen atom on one or more nitrogen atoms, then these are preferably pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridyl or N-oxypyridyl radicals.

Alkyl, alkoxy and alkylthio substituents in the heterocyclic five- and six-membered rings can contain up to 6 and preferably up to 4 carbon atoms, the methyl, ethyl, methoxy, ethoxy, methylthio and ethylthio radicals being preferred. By halogen, there is to be understood fluorine, chlorine or bromine, chlorine being preferred.

When $R_1$ signifies a phenyl ring of general formula (II), then the alkyl moiety of the substituents $R_3$, $R_4$ and $R_5$ can contain up to 5 and preferably up to 4 carbon atoms. Preferred substituents in this sense include, for example, methanesulphonyloxy, ethanesulphonyloxy, n-propanesulphonyloxy, isopropanesulphonyloxy, trifluoromethanesulphonyloxy, methylsulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-ethyl-n-propanesulphonylamino, N-n-propyl-n-propanesulphonylamino, N-methyl-trifluoromethanesulphonylamino, N-ethyltrifluoromethanesulphonylamino, N-isopropyl-trifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-n-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropyl-aminosulphonyl, acetylamino, propionylamino, methylaminocarbonylamino, ethylaminocarbonylamino, propylaminocarbonylamino, methyl, ethyl, propyl, methoxy, ethoxy, propoxy, allyloxy, but-2-enyloxy, but-3-enyloxy, pent-2-enyloxy, propargyloxy, but-2-ynyloxy, but-3-ynyloxy, cyanomethyloxy, cyanoethyloxy, methoxycarbonylmethoxy, methoxycarbonylethoxy, methylthio, ethylthio, methyl-sulphinyl, ethylsulphinyl, methylsulphonyl, ethyl-sulphonyl, dimethylaminocarbonylamino, diethylaminocarbonylamino, N-methyl-methylcarbonylamino, N-ethyl-methylcarbonylamino, N-methyl-ethylcarbonylamino, N-ethyl-ethylcarbonylamino, methoxysulphonyl and ethoxysulphonyl.

In the case of sulphonyl and carbonyl groups which can be substituted by imino groups, these are preferably morpholino-, pyrrolidino-, piperidino- and hexamethyleneimino radicals.

In particular, $R_3$ is preferably a hydrogen atom, an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by a hydroxyl, alkoxy, amino, alkylamino or dialkylamino group or a sulphonyl group substituted by an amino, dialkylamino or morpholino group, wherein each of the above-mentioned alkyl moieties can contain 1 or 2 carbon atoms, a nitro or cyano group or an alkylaminosulphonyl radical containing up to 4 carbon atoms, an alkylcarbonylamino, aminocarbonylamino or N-alkylaminocarbonylamino radical, an alkylthio, alkylsulphinyl or alkylsulphonyl radical, wherein each of the above-mentioned alkyl moieties can contain 1 to 2 carbon atoms, a halogen atom, an amino or hydroxyl group or a dialkylamino, alkyl, alkoxy, alkenyloxy or alkynyloxy radical with preferably up to 3 carbon atoms, a cyanomethoxy or methoxycarbonylmethoxy radical or a trifluoromethyl or 1-imidazolyl radical; $R_4$ is preferably a hydrogen atom, halogen preferably chlorine, an alkyl radical containing up to 3 carbon atoms preferably methyl, an alkoxy preerably methoxy or dialkylamino radical containing 1 or 2 carbon atoms in each alkyl moiety or a halogen atom and $R_5$ is preferably a hydrogen atom or a methoxy radical. The phenyl radical can contain 1 to 3 of the said substituents.

Preferred monosubstituted compounds include the hydroxyl, $C_1$–$C_3$-alkyl, trifluoromethyl, $C_1$–$C_3$-alkoxy, allyloxy, propargyloxy, cyanomethoxy, methoxycarbonylmethoxy, halogeno, nitro, amino, aminocarbonyl, methoxycarbonyl, $C_1$–$C_3$-dialkylamino, $C_1$–$C_3$-alkylthio, $C_1$–$C_3$ alkylsulphinyl, $C_1$–$C_3$-alkylsulphonyl, $C_1$–$C_3$-alkylsulphonyloxy and 1-imidazolyl compounds, the substituent being in the 2-, 3- or 4-position.

Preferred disubstituted compounds contain as substituents alkanesulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radicals, carbonyl groups substituted by a hydroxyl, alkoxy, amino, alkylamino or dialkylamino radicals or sulphonyl groups substituted by amino, dialkylamino or morpholino radicals, alkylaminosulphonyl, alkylcarbonylamino, aminocarbonylamino or N-alkyl-aminocarbonylamino radicals, hydroxyl, alkyl, alkoxy, allyloxy, propargyloxy, cyanomethoxy, methoxycarbonylmethoxy, cyano, halogeno, nitro, amino, dialkylamino, alkylthio, alkylsulphinyl, alkylsulphonyl or 1-imidazolyl radicals, wherein the two substituents can be the same or different and can be in the 2,3-, 2,4-, 2,5-, 2,6-, 3,4- or 3,5-positions but preferably in the 2,4-, 2,5- or 3,4-positions and the above-mentioned alkyl radicals, alone or in combination with other radicals, can contain up to 3 carbon atoms.

The preferred trisubstituted radical is the 3,4,5-trimethoxyphenyl radical.

When X is a valency bond, besides the above-mentioned groups, $R_1$ is also preferably a hydrogen atom, an alkyl radical containing up to 8 carbon atoms, an alkenyl or alkynyl radical containing 2 to 8 carbon atoms, a cycloalkyl radical containing 3 to 7 carbon atoms, a cycloalkenyl radical containing 5 or 6 carbon atoms, a $C_1$–$C_3$-althylthio, $C_1$–$C_4$-carboxyalkyl, alkoxycarbonylalkyl or alkoxyalkyl radical containing up to 4 carbon atoms in each of the said alkyl moieties, or a hydroxyl, mercapto, amino, pyridylcarbonylamino or trifluoromethyl radical. Especially preferred in this sense are the methyl, ethyl, n-propyl, isopropyl, pentyl, hexyl, sec.-butyl, tert.-butyl, prop-1-enyl, prop-1-ynyl, prop-2-enyl, cyclopropyl, cyclobutyl, cyclopentyl, cyclohexyl, cyclopent-1-enyl, methoxymethyl, ethoxycarbonylethyl, carboxyethyl, hydroxyl, mercapto, methylthio, ethylthio, n-propylthio, amino, pyridylcarbonylamino and trifluoromethyl radicals.

X is preferably a valency bond or a methylene, ethylene or vinylene radical.

A is preferably an oxygen or sulphur atom or an

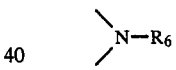

group, in which $R_6$ is preferably a hydrogen atom or a methyl, ethyl, propyl, isopropyl, butyl, 2-butyl or 2-(2-methyl)propyl radical.

$R_2$ is preferably a hydrogen atom or a methyl, ethyl, propyl, butyl, 2-propyl, 2-butyl, 2-(2-methyl)propyl, hydroxyl, amino, mercapto, $C_1$–$C_3$-alkylcarbonylamino, $C_1$–$C_3$-alkylaminocarbonyl, aminocarbonylamino, pyridylcarbonylamino or $C_1$–$C_3$-alkylthio radical.

Especially preferred compounds are those of general formula (I) wherein $R_1$ is a pyrrole, furan, thiophene, pyrazole, imidazole, thiazole, isothiazole, oxazole, isoxazole, triazole, tetrazole, thiadiazole, oxadiazole, pyridine, N-oxypyridine, pyrazine, N,N-dioxypyrazine, pyrimidine, N,N-dioxypyrimidine, pyridazine, oxazine, thiazine, triazine or tetrazine radical, as well as a methyl, ethyl, methoxy, ethoxy, methylthio, ethylthio or chlorine-substituted derivative thereof, or is a phenyl radical of general formula (II) in which $R_3$ is a hydrogen atom or a methanesulphonyloxy, trifluoromethanesulphonyloxy, methanesulphonylamino, trifluoromethanesulphonylamino, methanesulphonylmethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl radical, $R_4$ is a hydrogen or chlorine atom or a methyl, methoxy or dimethylamino radical and $R_5$ is a hydrogen atom or a methoxy radical; or, when X is a valency bond, besides the above-mentioned groups, $R_1$ is also a hydrogen atom, a methyl, ethyl, propyl, isopropyl, butyl, 2-butyl, tert.-butyl, pentyl, hexyl, prop-2-enyl, prop-1-enyl, prop-1-ynyl, cyclopropyl, cyclobutyl, cyclopentyl, cyclopent-1-enyl, methoxymethyl, ethoxycarbonylethyl, carboxyethyl, hydroxyl, mercapto, methylthio, amino, pyridylcarbonylamino or trifluoromethyl radical, X is a valency bond, an alkylene radical containing 1 or 2 carbon atoms or a vinylene radical, A is an oxygen or sulphur atom or an

group, in which $R_6$ is a hydrogen atom or a methyl, ethyl, propyl or isopropyl radical and $R_2$ is a hydrogen atom or a methyl, ethyl, propyl, butyl, isopropyl, 2-butyl, tert.-butyl, hydroxyl, amino, mercapto, methylthio, methylcarbonylamino, pyridylcarbonylamino, methylaminocarbonylamino or aminocarbonylamino radical.

The compounds of general formula (I) can be prepared according to the following schemes 1–4:

Scheme 1

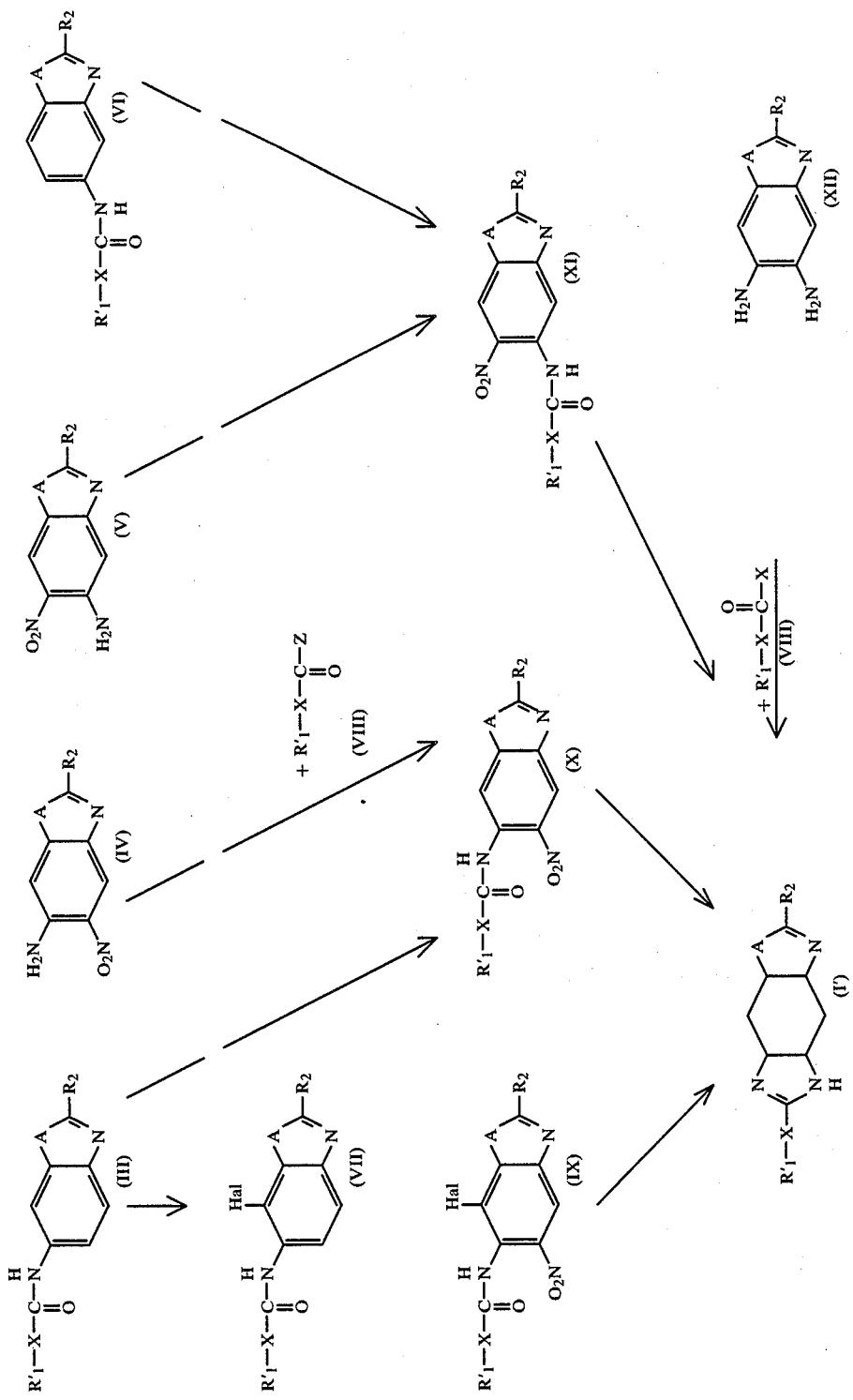

As can be seen from scheme 1, compounds of general formulae (III) and (VI) can be converted by nitration into compounds of general formulae (X) and (XI) which, after reduction of the nitro group and ring closure, give compounds of general formula (I'), wherein A, X and $R_2$ have the same meanings as above and $R'_1$ is a heterocyclic five-membered ring containing 1 to 4 heteroatoms or a heterocyclic six-membered ring containing 1 to 5 heteroatoms, wherein the heteroatoms in the said five- and six-membered rings can be the same or different and signify nitrogen, oxygen or sulphur atoms and one or more nitrogen atoms can optionally carry an oxygen atom, and the said five- and six-membered rings can optionally be substituted by one or more alkyl, alkoxy, alkylthio, hydroxyl, nitro, amino, halogen or cyano radicals, or is a phenyl ring of the general formula:

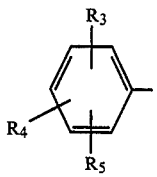

(II)

wherein $R_3$, $R_4$ and $R_5$, which can be the same or different, are hydrogen atoms or alkanesulphonyloxy, trifluoromethylsulphonyloxy, alkanesulphonylamino, trifluoromethanesulphonylamino, N-alkyl-alkanesulphonylamino, N-alkyltrifluoromethanesulphonylamino, alkylsulphenylmethyl, alkylsulphinylmethyl or alkylsulphonylmethyl radicals or are carbonyl groups substituted by a hydroxyl, alkoxy, amino, alkylamino or dialkylamino radical or are sulphonyl groups substituted by an amino, alkylamino, dialkylamino or cyclic imino group, whereby a methylene group can be replaced by a sulphur or oxygen atom, or are alkylcarbonylamino, aminocarbonylamino, alkylaminocarbonylamino, alkylthio, alkylsulphinyl, alkylsulphonyl, alkenyloxy, alkynyloxy, cyanoalkoxy, carboxyalkoxy, alkoxycarbonylalkoxy, nitro, halogen, amino, hydroxyl, alkyl, alkoxy, dialkylamino, 1-imidazolyl, trifluoromethyl or cyano radicals or, when X is a valency bond, besides the said groups, $R'_1$ can also be an alkyl, alkenyl, alkynyl, cycloalkyl, cycloalkenyl, halogenoalkyl, carboxyalkyl, alkoxycarbonylalkyl or alkoxyalkyl radical.

In some cases, it is preferable to protect a reactive position in the phenyl moiety of the compounds (III) by the preparation of compounds of general formula (VII), wherein $R'_1$, X, $R_2$ and A have the above-given meanings and Hal is a halogen atom, preferably a bromine atom. After nitration, there are obtained compounds of general formula (IX) which, after reduction of the nitro group, with the simultaneous splitting off of Hal, give compounds of general formula (I').

The compounds (X) and (XI), which are important as intermediates, are obtained by reaction of compounds of general formulae (IV) and (V) with compounds of general formula (VIII), wherein $R'_1$, X, A and $R_2$ have the above-given meanings and Z is a group which is easily split off.

Finally, compounds of general formula (I') can also be prepared by direct reaction of compounds of general formula (XII) with compounds of general formula (VIII), wherein $R'_1$, X, Z, A and $R_2$ have the above-given meanings.

In particular, compounds of general formula (VIII) are to be understood to be aldehydes, as well as acid halides, such as acid chlorides, carboxylic acid esters, such as methyl and ethyl esters, and other activated carboxylic acid derivatives, for example anhydrides, as well as the carboxylic acids themselves.

If the compound of general formula (VIII) is an aldehyde, the reaction to give a Schiff's base with a compound of general formula (XII) preferably takes place in an alcoholic medium, the subsequent cyclisation and oxidation to give a compound of general formula (I') taking place by heating the reaction mixture to reflux in the presence of atmospheric oxygen and a catalytic amount of an acid, for example toluenesulphonic acid.

If the compound of general formula (VIII) is a carboxylic acid, then the reaction with a compound of general formula (IV), (V) or (XII) to give an amide takes place in the presence of a water-removing agent, preferably polyphosphoric acid, at a temperature of from 50° to 250° C. and preferably of from 100° to 200° C.

If the compound of general formula (VIII) is a carboxylic acid derivative, the reaction with a compound of general formula (IV), (V) or (XII) to give an amide takes place in an inert solvent, preferably in methylene chloride or pyridine, and the subsequent cyclisation to give a compound of general formula (I') is carried out, after previous hydrogenation of the nitro group in the compound of general formula (X) or (XI) or in a compound of general formula (IX), with simultaneous splitting off of Hal, in a solvent or solvent mixture, for example, ethanol, isopropanol, glacial acetic acid, benzene, chlorobenzene, glycol, diethyleneglycol dimethyl ether, sulfolan or dimethylformamide, at a temperature of from 0° to 250° C. and preferably at the boiling temperature of the reaction mixture, optionally in the presence of a condensation agent, for example phosphorus oxychloride, thionyl chloride, p-toluenesulphonic acid, hydrochloric acid, sulphuric acid, phosphoric acid or polyphosphoric acid, or preferably also in the presence of a base, for example sodium hydroxide, potassium methylate or potassium tert.-butylate. However, the cyclisation can also be carried out without the use of solvents and/or condensation agents.

The above-mentioned hydrogenation of the nitro group is preferably carried out in a solvent, for example water, ethanol, glacial acetic acid, ethyl acetate or dimethylformamide, preferably with hydrogen in the presence of a hydrogenation catalyst, for example Raney nickel, platinum or palladium/charcoal, or with a metal, such as iron, tin or zinc, in the presence of an acid, or with a salt, such as ferrous sulphate, stannous chloride, sodium sulphide, sodium hydrogen sulphide or sodium dithionite, or with hydrazine in the presence of Raney nickel, at a temperature of from 0° to 250° C. but preferably at ambient temperature.

The compounds of general formulae (III), (IV), (V), (VI) and (XII) are known from the literature or can easily be prepared by processes known from the literature. The compounds of general formulae (VII), (IX), (X) and (XI) are new and also the subject of the present invention.

As can be seen from Scheme 2, compounds of general formula (I''), in which $R_2$ and A have the above-given meanings and $R''_1$ is a hydroxyl, mercapto or amino group, can be prepared by processes known from the literature by ring closure of compounds of general formula (XII) with reagents such as urea, phosgene, thiophosgene, carbonyl diimidazole or cyanogen bromide.

Scheme 2

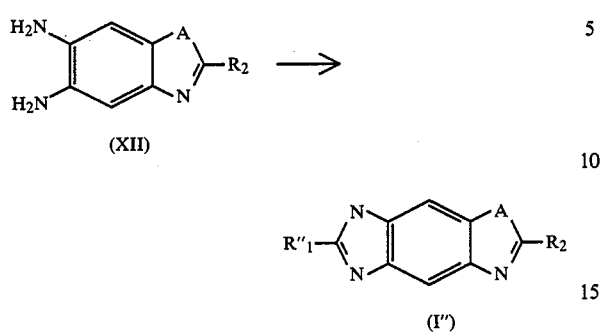

(cf. in this regard: E. S. Schipper and A. R. Day in R. C. Elderfield (ed.), Heterocyclic Compounds, Vol. 5, pub. John Wiley & Sons, New York, 1957, p. 284; J. W. Cornforth, ebenda, p. 439; J. M. Sprague, A. H. Land, ebenda, p. 548).

These reactions are preferably carried out in a solvent or solvent mixture, for example, benzene, toluene, chlorobenzene, dimethylformamide, methylene chloride or aqueous hydrochloric acid, at a temperature of from −20° to +100° C. and preferably at ambient temperature.

The ring closures illustrated in Scheme 2 are equally applicable to compounds of general formula (XIII), in which case compounds of general formula (I''') are obtained, wherein $R_1$, X and A have the above-given meanings and $R'_2$ is a hydroxyl, mercapto or amino group (Scheme 3):

Scheme 3

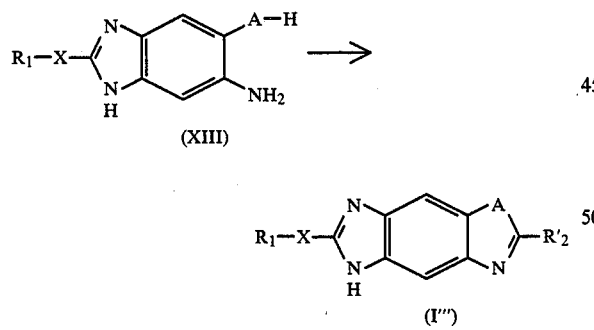

As can be seen from Scheme 4, compounds of general formula (I''''), wherein $R_1$, X and A have the above-given meanings and $R''_2$ is a hydrogen atom or an alkyl radical, can be prepared by reacting compounds of general formula (XIII) with compounds of general formula (XIV), wherein $R''_2$ is a hydrogen atom or an alkyl radical and Y is a residue which is easily split off. (cf.: E. S. Schipper and A. R. Day, in R. C. Elderfield (ed.), Heterocyclic Compounds, Vol. 5, publ. J. Wiley & Sons, New York, 1957, p. 274; J. W. Cornforth, ebenda, p. 418; J. M. Sprague, A. H. Land, ebenda, p. 506).

Scheme 4

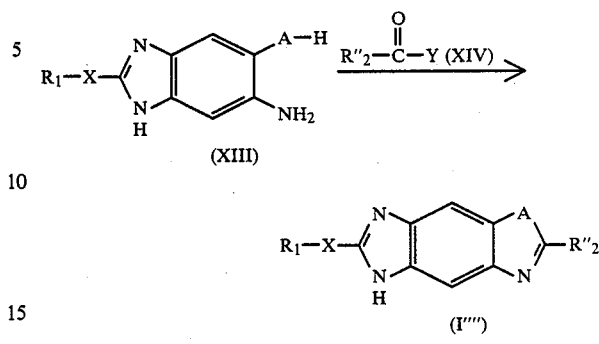

Compounds of general formula (I) can also be subsequently converted into other compounds of general formula (I). This applies, for example:

(a) For the oxidation of a five- or six-membered ring with one or more nitrogen atoms to give the corresponding N-oxides. The oxidation is preferably carried out with one or more equivalents of the oxidation agent employed, for example with hydrogen peroxide in glacial acetic acid, trifluoroacetic acid or formic acid at a temperature of from 20° to 100° C. or in acetone at a temperature of from 0° to 60° C. or with a peracid, for example performic acid or m-chloroperbenzoic acid, in glacial acetic acid, trifluoroacetic acid, methylene chloride or chloroform, at a temperature of from 0° to 60° C.

(b) For the hydrogenation of a vinylene compound (X=—CH=CH—) into the corresponding ethylene compound (X=—$CH_2$—$CH_2$—). The hydrogenation is preferably carried out in a solvent, for example water, water/ethanol, methanol, glacial acetic acid, ethyl acetate or dimethylformamide, preferably with hydrogen in the presence of a hydrogenation catalyst, for example Raney nickel, platinum or palladium/charcoal.

(c) For the preparation of a compound of general formula (I), wherein $R_3$ is an alkylsulphinyl, alkylsulphonyl, alkylsulphinylmethyl or alkylsulphonylmethyl radical, by subsequent oxidation of a compound of the general formula:

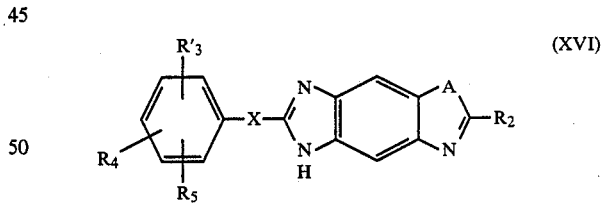

wherein $R_2$, A, $R_4$, $R_5$ and X have the above-given meanings and $R'_3$ is an alkylthio, alkylsulphinyl, alkylsulphinylmethyl or alkylsulphenylmethyl radical with, in each case, up to 3 carbon atoms in the alkyl moiety.

The oxidation is preferably carried out in a solvent or solvent mixture, for example in water, water/pyridine, acetone, glacial acetic acid, dilute sulphuric acid or trifluoroacetic acid, depending upon the oxidation agent used at a temperature of from −80° to 100° C.

For the preparation of an alkylsulphinyl or alkylsulphinylmethyl compound of general formula (I), the oxidation is preferably carried out with one equivalent of the oxidation agent employed, for example with hydrogen peroxide in glacial acetic acid, trifluoroacetic acid or formic acid, at a temperature of from 0° to 20° C.

or in acetone at a temperature of from 0° to 60° C. or with a per acid, for example performic acid, in glacial acetic acid or trifluoroacetic acid at a temperature of from 0° to 50° C. or with m-chloroperbenzoic acid in methylene chloride or chloroform at a temperature of from −20° to +60° C. or with sodium metaperiodate in aqueous methanol or ethanol at a temperature of from −15° to +25° C. or with bromine in glacial acetic acid or aqueous acetic acid or with N-bromosuccinimide in ethanol or with tert.-butyl hypochlorite in methanol at a temperature of from −80° to −30° C. or with iodobenzodichloride in aqueous pyridine at a temperature of from 0° to 50° C. or with nitric acid in glacial acetic acid at a temperature of from 0° to 20° C. or with chromic acid in glacial acetic acid or acetone at a temperature of from 0° to 20° C. or with sulphuryl chloride in methylene chloride at a temperature of −70° C., the thioether-chlorine complex hereby obtained being preferably hydrolysed with aqueous ethanol.

For the preparation of an alkylsulphonyl or alkylsulphonylmethyl compound of general formula (I), the oxidation is preferably carried out, respectively, with one or with two or more equivalents of the oxidation agent employed, for example hydrogen peroxide in glacial acetic acid, trifluoroacetic acid or formic acid, at a temperature of from 20° to 100° C. or in acetone at a temperature of from 0° to 60° C. or with a per acid, such as performic acid or m-chloroperbenzoic acid, in glacial acetic acid, trifluoroacetic acid, methylene chloride or chloroform, at a temperature of from 0° to 60° C. or with nitric acid in glacial acetic acid at a temperature of from 0° to 20° C. or with chromic acid or potassium permanganate in glacial acetic acid, water/sulphuric acid or in acetone at a temperature of from 0° to 20° C.

The preparation of compounds of general formula (I), wherein $R_3$ is an alkanesulphonyloxy, trifluoromethanesulphonyloxy, alkanesulphonylamino, N-alkylalkanesulphonylamino, trifluoromethanesulphonylamino or N-alkyltrifluoromethanesulphonylamino radical, is achieved by the subsequent reaction of a compound of the general formula:

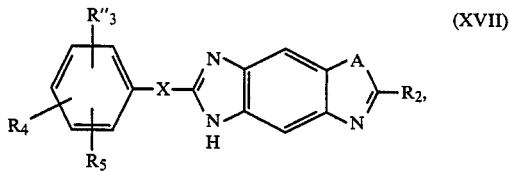

(XVII)

wherein $R_2$, A, $R_4$, $R_5$ and X have the same meanings as above and $R''_3$ is a hyroxyl or amino group or an N-alkylamino radical with up to 3 carbon atoms in the alkyl moiety, with a sulphonic acid of the general formula:

$R_7\text{—}SO_2OH$ (XVIII)

in which $R_7$ is an alkyl radical containing up to 3 carbon atoms or a trifluoromethyl radical, in the presence of a water-removing agent and/or of an agent activating the acid or the amine or with a reactive derivative thereof.

The reaction is preferably carried out in a solvent or solvent mixture, for example methylene chloride, diethyl ether, tetrahydrofuran, dioxan or benzene, optionally in the presence of an acid-binding agent, for example sodium carbonate, triethylamine or pyridine, whereby the two latter agents can also be used as solvents, in the presence of an agent activating the acid or removing water, for example thionyl chloride or phosphorus pentachloride, but preferably with a reactive derivative of a compound of general formula (XVIII), for example with an anhydride or halide, for example methanesulphonic acid chloride or ethanesulphonic acid chloride, preferably at a temperature of from 0° to 100° C., for example at a temperature of from ambient temperature to 50° C.

The preparation of compounds of general formula (I), wherein $R_3$ is a carbonyl or sulphonyl group substituted by an amino, alkylamino, dialkylamino or hydrazino group, is achieved by the subsequent reaction of a compound of the general formula:

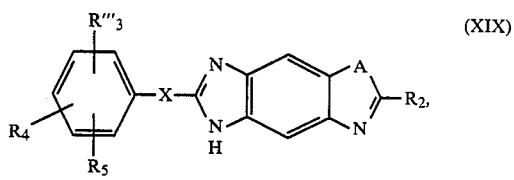

(XIX)

wherein $R_2$, $R_4$, $R_5$, A and X have the above-given meanings and $R'''_3$ is a carboxyl or hydroxysulphonyl group, or a reactive derivative thereof, for example an ester or acid chloride, with hydrazine, a cyclic amine or an amine of the general formula:

$R_8\text{—NH—}R_9$ (XX), wherein $R_8$ and $R_9$, which can be the same or different, are hydrogen atoms or alkyl radicals containing up to 5 carbon atoms, or with a reactive derivative thereof when $R'''_3$ is a carboxyl or hydroxysulphonyl group.

The reaction is preferably carried out in a solvent or solvent mixture, for example methylene chloride, ethanol, chloroform, carbon tetrachloride, diethyl ether, tetrahydrofuran, dioxan, benzene, toluene, acetonitrile or dimethylformamide, optionally in the presence of an agent activating the acid or removing water, for example in the presence of ethyl chloroformate, thionyl chloride, phosphorus trichloride, phosphorus pentoxide, N,N'-dicyclohexylcarbodiimide/N-hydroxysuccinimide, N,N'-carbonyldiimidazole or N,N'-thionyldiimidazole or triphenylphosphine/carbon tetrachloride, or of an agent activating the hydrazino or amino group, for example phosphorus trichloride, and optionally in the presence of an inorganic base, for example sodium carbonate, or of a tertiary organic base, for example triethylamine or pyridine, which can simultaneously serve as a solvent, at a temperature of from −25° to +250° C. but preferably at a temperature of from −10° C. to the boiling temperature of the solvent used. Furthermore, water formed during the reaction can be removed by azeotropic distillation, for example by heating with toluene on a water separator, or by the addition of a drying agent, for example anhydrous magnesium sulphate or a molecular sieve.

However, the reaction is carried out especially advantageously in an appropriate halide, for example the carboxylic acid or sulphonic acid chloride, and hydrazine or an appropriate amine, whereby these can simultaneously serve as solvents, at a temperature of from 0° to 50° C.

If a compound is obtained of general formula (I), wherein $R_3$ is a cyano group, this can subsequently be converted by means of alcoholysis and/or hydrolysis into a corresponding compound in which $R_3$ is an alkoxycarbonyl radical containing a total of 2 to 5 carbon atoms, an aminocarbonyl or carboxyl group and/or $R_4$ is an alkoxycarbonyl radical with a total of 2 to 4 carbon atoms, an aminocarbonyl or carboxyl group, and/or a compound of general formula (I), wherein $R_3$ is a carboxyl group, can be converted by esterification into a corresponding compound of general formula (I), wherein $R_3$ is an alkoxycarbonyl radical with a total of 2 to 5 carbon atoms.

The subsequent alcoholysis and/or hydrolysis is preferably carried out either in the presence of an acid, for example hydrochloric acid, sulphuric acid, phosphoric acid or trichloroacetic acid, or in the presence of a base, for example sodium hydroxide or potassium hydroxide, in an appropriate solvent, for example water, water/methanol, ethanol, water/ethanol, water/isopropanol or water/dioxan, at a temperature of from $-10°$ to $+120°$ C., for example at a temperature of from ambient temperature to the boiling temperature of the reaction mixture.

The subsequent esterification is preferably carried out in an appropriate solvent, for example in an appropriate alcohol, pyridine, toluene, methylene chloride, tetrahydrofuran or dioxan, in the presence of an acid-activating and/or water-removing agent, for example thionyl chloride, ethyl chloroformate, N,N'-dicyclohexylcarbodiimide or an isourea ether thereof, optionally in the presence of a reaction accelerator, for example copper chloride, or by reaction, for example, with an appropriate carbonic acid diester, at a temperature of from 0° to 100° C. but preferably at a temperature of from 20° C. to the boiling point of the solvent in question.

(d) For the reaction of a compound of general formula (I), wherein $R_2$ is a hydroxyl group or X is a valency bond and $R_1$ is a hydroxyl group or in which not only $R_1$ but also $R_2$ is a hydroxyl group and X is a valency bond, to give another compound of general formula (I), wherein $R_1$ and/or $R_2$ is a mercapto group.

The reaction is carried out by processes known from the literature with a reagent transferring a sulphur atom, for example phosphorus pentasulphide, there preferably being used 1 to 5 mole but more preferably 1 mole of phosphorus pentasulphide in an appropriate solvent. As solvent, there can be used, for example, tetrahydrofuran, dioxan, benzene, toluene or pyridine at a temperature of from 25° to 125° C. There is here preferred a reaction period of from 1 to 10 and preferably of 5 hours, depending upon the reaction components.

(e) For the reaction of a compound of general formula (I), wherein $R_2$ is an amino group or in which $R_1$ is an amino group (X being a valency bond) or in which X is a valency bond and not only $R_1$ but also $R_2$ is an amino group, with an activated acid derivative, for example an anhydride or acid halide, to give an alkylcarbonylamino or pyridylcarbonylamino derivative. The reactions are preferably carried out in an inert solvent, for example methylene chloride or pyridine, at a temperature of from 0° to 250° C. but preferably at the boiling temperature of the solvent.

(f) For the subsequent alkylation of a compound of general formula (I), wherein $R_2$ is a mercapto group or in which $R_1$ is a mercapto group and X a valency bond or wherein X is a valency bond and not only $R_1$ but also $R_2$ is a mercapto group, to give a corresponding alkylthio compound. The reactions are preferably carried out in a solvent, for example acetone, diethyl ether, benzene, toluene, dimethylformamide, at a temperature of from $-30°$ to $+100°$ C. but preferably at ambient temperature in the presence of a base, for example potassium carbonate or sodium hydride, and of an alkylation agent, for example an alkyl halide or alkyl sulphate.

Furthermore, if desired, the compounds obtained of general formula (I) can be subsequently converted into their physiologically acceptable acid-addition salts with inorganic or organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned initially, the new compounds of general formula (I), their tautomers and their physiologically acceptable acid-addition salts, in the case of a long period of action, display superior physiological properties, especially a blood pressure-lowering and/or positive inotropic action and/or they influence the thrombocyte function and improve the microcirculation.

For the preparation of pharmaceutical compositions, the compounds according to the present invention are mixed in the usual manner with appropriate pharmaceutical carrier substances, aroma, flavouring and colouring materials and formed, for example, into tablets or dragees or, with the addition of appropriate adjuvants, are suspended or dissolved in water or an oil, for example olive oil.

The new compounds according to the present invention can be administered enterally or parenterally in liquid or solid form. As injection medium, it is preferred to use water which contains the conventional additives for injection solutions, such as stabilising agents, solubilising agents or buffers.

Such additives include, for example, tartrate and citrate buffers, ethanol, complex formers (such as ethylenediamine-tetraacetic acid and the non-toxic salts thereof) and high molecular weight polymers (such as polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, contain flavouring and sweetening agents.

The compounds according to the present invention are usually administered in amounts of from 10 to 500 mg. per day, referred to a body weight of 75 kg. It is preferred to administer 1 to 2 tablets with an active material content of 5 to 200 mg. 2 or 3 times per day. The tablets can also be retarded, in which case it is only necessary to administer 1 or 2 tablets with 10 to 500 mg. of active material once per day. The active material can also be administered by injection 1 to 8 times per day or by continuous infusion, in which case amounts of from 5 to 200 mg. per day normally suffice.

Apart from the compounds described in the following Examples, preferred compounds according to the present invention include the following, as well as the tautomers thereof:

6-(4-methoxyphenyl)-1-methyl-1,2,3,5-tetrahydrobenzo[1,2-d:4,5-d']diimidazol-2-one 6-(4-nitrophenyl)-1-methyl-1,2,3,5-tetrahydrobenzo[1,2-d:4,5-d']diimidazol-2-one 6-(4-aminophenyl)-1-methyl-1,2,3,5-tetrahydrobenzo[1,2-d:4,5-d']diimidazol-2-one 6-(4-acetylaminophenyl)-1-methyl-1,2,3,5-tetrahydrobenzo[1,2-d:4,5-d']diimidazol-2-one
6-(4-hydroxyphenyl)-1-methyl-1,2,3,5-tetrahydrobenzo[1,2-d:4,5-d']diimidazol-2-one
6-(4-chlorophenyl)-1-methyl-1,2,3,5-tetrahydrobenzo[1,2-d:4,5-d']diimidazol-2-one
6-(4-methylsulphenyl-2-methoxyphenyl)-1-methyl-1,2,3,5-tetrahydrobenzo[1,2-d:4,5-d']diimidazol-2-one
6-(4-methylsulphinyl-2-methoxyphenyl)-1-methyl-1,2,3,5-tetrahydrobenzo[1,2-d:4,5-d']diimidazol-2-one
6-(4-methylsulphonyl-2-methoxyphenyl)-1-methyl-1,2,3,5-tetrahydrobenzo[1,2-d:4,5-d']diimidazol-2-one
6-(4-methylsulphonyloxy-2-methoxyphenyl)-1-methyl-1,2,3,5-tetrahydrobenxo[1,2-d:4,5-d']diimidazol-2-one
6-(4-aminosulphonyl-2-methoxyphenyl)-1-methyl-1,2,3,5-tetrahydrobenzo[1,2-d:4,5-d']diimidazol-2-one
6-(4-methylsulphenylmethyl-2-methoxyphenyl)-1-methyl-1,2,3,5-tetrahydrobenzo[1,2-d:4,5-d']diimidazol-2-one
6-(4-methylsulphinylmethyl-2-methoxyphenyl)-1-methyl-1,2,3,5-tetrahydrobenzo[1,2-d:4,5-d']diimidazol-2-one
6-(4-methylsulphonylmethyl-2-methoxyphenyl)-1-methyl-1,2,3,5-tetrahydrobenzo[1,2-d:4,5-d']diimidazol-2-one
6-(N-oxy-4-pyridyl)-1-methyl-1,2,3,5-tetrahydrobenzo[1,2-d:4,5-d']diimidazol-2-one
6-(N-oxy-3-pyridyl)-1-methyl-1,2,3,5-tetrahydrobenzo[1,2-d:4,5-d']diimidazol-2-one
6-(2-chloro-4-pyridyl)-1-methyl-1,2,3,5-tetrahydrobenzo[1,2-d:4,5-d']diimidazol-2-one
6-(2-hydroxy-4-pyridyl)-1-methyl-1,2,3,5-tetrahydrobenzo[1,2-d:4,5-d']diimidazol-2-one
6-(2-methyl-4-pyridyl)-1-methyl-1,2,3,5-tetrahydrobenzo[1,2-d:4,5-d']diimidazol-2-one
6-[(4-pyridyl)-2-ethyl]-1-methyl-1,2,3,5-tetrahydrobenzo[1,2-d:4,5-d']diimidazol-2-one
6-[(4-pyridyl)-2-ethenyl]-1-methyl-1,2,3,5-tetrahydrobenzo[1,2-d:4,5-d']diimidazol-2-one
6-(1,2,5-thiadiazolyl)-1-methyl-1,2,3,5-tetrahydrobenzo[1,2-d:4,5-d']diimidazol-2-one
6-(1,3,4-thiadiazolyl)-1-methyl-1,2,3,5-tetrahydrobenzo[1,2-d:4,5-d']diimidazol-2-one
6-propyl-1-methyl-1,2,3,5-tetrahydrobenzo[1,2-d:4,5-d']diimidazol-2-one
6-trifluoromethyl-1-methyl-1,2,3,5-tetrahydrobenzo[1,2-d:4,5-d']diimidazol-2-one
6-hexyl-1-methyl-1,2,3,5-tetrahydrobenzo[1,2-d:4,5-d']diimidazol-2-one
6-(2-propyl)-1-methyl-1,2,3,5-tetrahydrobenzo[1,2-d:4,5-d']diimidazol-2-one
6-(2-propenyl)-1-methyl-1,2,3,5-tetrahydrobenzo[1,2-d:4,5-d']diimidazol-2-one
6-cyclopropyl-1-methyl-1,2,3,5-tetrahydrobenzo[1,2-d:4,5-d']diimidazol-2-one
6-cyclohexyl-1-methyl-1,2,3,5-tetrahydrobenzo[1,2-d:4,5-d']diimidazol-2-one
6-cyclopentenyl-1-methyl-1,2,3,5-tetrahydrobenzo[1,2-d:4,5-d']diimidazol-2-one
6-mercapto-1-methyl-1,2,3,5-tetrahydrobenzo[1,2-d:4,5-d']diimidazol-2-one
6-methylthio-1-methyl-1,2,3,5-tetrahydrobenzo[1,2-d:4,5-d']diimidazol-2-one
6-amino-1-methyl-1,2,3,5-tetrahydrobenzo[1,2-d:4,5-d']diimidazol-2-one
6-(4-pyridylcarbonylamino)-1-methyl-1,2,3,5-tetrahydrobenzo[1,2-d:4,5-d']diimidazol-2-one
6-(2-carboxyethyl)-1-methyl-1,2,3,5-tetrahydrobenzo[1,2-d:4,5d']diimidazol-2-one
6-(2-ethoxycarbonylethyl)-1-methyl-1,2,3,5-tetrahydrobenzo[1,2-d:4,5-d']diimidazol-2-one
6-methoxymethyl-1-methyl-1,2,3,5-tetrahydrobenzo[1,2-d:4,5-d']diimidazol-2-one
6-(2-pyridyl)-1-ethyl-1,2,3,5-tetrahydrobenzo[1,2-d:4,5-d']diimidazol-2-one
6-(N-oxy-4-pyridyl)-1-ethyl-1,2,3,5-tetrahydrobenzo[1,2-d:4,5-d']diimidazol-2-one
6-(3-pyridazinyl)-1-ethyl-1,2,3,5-tetrahydrobenzo[1,2-d:4,5-d']diimidazol-2-one
6-(1,2,5-thiadiazol-3-yl)-1-ethyl-1,2,3,5-tetrahydrobenzo[1,2-d:4,5-d']diimidazol-2-one
6-(1,3,4-thiadiazol-2-yl)-1-ethyl-1,2,3,5-tetrahydrobenzo[1,2-d:4,5-d']diimidazol-2-one
6-phenyl-1-ethyl-1,2,3,5-tetrahydrobenzo[1,2-d:4,5-d']diimidazol-2-one
6-(2-dimethylamino-4-nitrophenyl)-1-ethyl-1,2,3,5-tetrahydrobenzo[1,2-d:4,5-d']diimidazol-2-one
6-(4-trifluoromethylsulphonyloxy-2-methoxyphenyl)-1-ethyl-1,2,3,5-tetrahydrobenzo[1,2-d:4,5-d']diimidazol-2-one
6-[4-(4-morpholinylsulphonyl)-2-methoxyphenyl]-1-ethyl-1,2,3,5-tetrahydrobenzo[1,2-d:4,5-d']diimidazol-2-one
6-(4-carboxy-2-methoxyphenyl)-1-ethyl-1,2,3,5-tetrahydrobenzo[1,2-d:4,5-d']diimidazol-2-one
6-(4-ethoxycarbonyl-2-methoxyphenyl)-1-ethyl-1,2,3,5-tetrahydrobenzo[1,2-d:4,5-d']diimidazol-2-one
6-(4-aminocarbonyl-2-methoxyphenyl)-1-ethyl-1,2,3,5-tetrahydrobenzo[1,2-d:4,5-d']diimidazol-2-one
6-(4-cyano-2-methoxyphenyl)-1-ethyl-1,2,3,5-tetrahyrobenzo[1,2-d:4,5-d']diimidazol-2-one
6-(3,4,5-trimethoxyphenyl)-1-ethyl-1,2,3,5-tetrahydrobenzo[1,2-d:4,5-d']diimidazol-2-one
6-(2-furyl)-1-methyl-1,2,3,5-tetrahydrobenzo[1,2-d:4,5-d']diimidazol-2-one
6-(2-thienyl)-1-methyl-1,2,3,5-tetrahydrobenzo[1,2-d:4,5-d']diimidazol-2-one
6-(2-pyrrolyl)-1-methyl-1,2,3,5-tetrahydrobenzo[1,2-d:4,5-d']diimidazol-2-one
6-(4-imidazolyl)-1-methyl-1,2,3,5-tetrahydrobenzo[1,2-d:4,5-d']diimidazol-2-one
6-(4-pyrimidinyl)-1-methyl-1,2,3,5-tetrahydrobenzo[1,2-d:4,5-d']diimidazol-2-one
6-(5-pyrimidinyl)-1-methyl-1,2,3,5-tetrahydrobenzo[1,2-d:4,5-d']diimidazol-2-one
6-(1,2,4-triazol-3-yl)-1-methyl-1,2,3,5-tetrahydrobenzo[1,2-d:4,5-d']diimidazol-2-one
6-(1,2,4,5-tetrazin-3-yl)-1-methyl-1,2,3,5-tetrahydrobenzo[1,2-d:4,5-d']diimidazol-2-one
6-(2-methyl-5-pyrimidinyl)-1-methyl-1,2,3,5-tetrahydrobenzo[1,2-d:4,5-d']diimidazol-2-one
6-(2-hydroxy-5-pyrimidinyl)-1-methyl-1,2,3,5-tetrahydrobenzo[1,2-d:4,5-d']diimidazol-2-one
6-(1,2-dihydro-1-methyl-2-oxo-5-pyrimidinyl)-1-methyl-1,2,3,5-tetrahydrobenzo[1,2-d:4,5-d']diimidazol-2-one
6-(6-methyl-4-pyrimidinyl)-1-methyl-1,2,3,5-tetrahydrobenzo[1,2-d:4,5-d']diimidazol-2-one
6-(3-hydroxy-6-pyridazinyl)-1-methyl-1,2,3,5-tetrahydrobenzo[1,2-d:4,5-d']diimidazol-2-one
6-(5,6-dimethyl-1,2,4-triazin-3-yl)-1-methyl-1,2,3,5-tetrahydrobenzo[1,2-d:4,5-d']diimidazol-2-one
6-(3-methyl-5-pyrazolyl)-1-methyl-1,2,3,5-tetrahydrobenzo[1,2-d:4,5-d']diimidazol-2-one 6-(2-methyl-4-oxazolyl)-1-methyl-1,2,3,5-tetrahydrobenzo[1,2-d:4,5-d']diimidazol-2-one
6-(2,6-dihydroxy-4-pyrimidinyl)-1-methyl-1,2,3,5-tetrahydrobenzo[1,2-d:4,5-d']diimidazol-2-one
6-(2-pyrrolyl)-1-propyl-1,2,3,5-tetrahydrobenzo[1,2-d:4,5-d']diimidazol-2-one
6-(3-pyridyl)-1-propyl-1,2,3,5-tetrahydrobenzo[1,2-d:4,5-d']diimidazol-2-one
6-phenyl-1-propyl-1,2,3,5-tetrahydrobenzo[1,2-d:4,5-d']diimidazol-2-one
6-(4-methylaminocarbonylamino-2-methoxyphenyl)-1-propyl-1,2,3,5-tetrahydrobenzo[1,2-d:4,5-d']diimidazol-2-one
6-(4-aminocarbonylamino-2-methoxyphenyl)-1-propyl-1,2,3,5-tetrahydrobenzo[1,2-d:4,5-d']diimidazol-2-one
6-(4-methylaminocarbonylamino-2-methoxyphenyl)-1-propyl-1,2,3,5-tetrahydrobenzo[1,2-d:4,5-d']diimidazol-2-one
6-(4-pyridyl)-1-methyl-1,2,3,5-tetrahydrobenzo[1,2-d:4,5-d']diimidazol-2-thione
6-(4-pyridyl)-2-methyl-1,5-dihydrobenzo[1,2-d:4,5-d']diimidazole
6-(4-pyridyl)-1,2-dimethyl-1,5-dihydrobenzo[1,2-d:4,5-d']diimidazole
6-(4-pyridyl)-5H-imidazo-[4,5-f]benzoxazole
6-(5-pyrimidinyl)-2,3-dihydro-5H-imidazo[4,5-f]benzoxazol-2-one
6-(2-chloro-4-pyridyl)-2,3-dihydro-5H-imidazo[4,5-f]benzoxazol-2-one
6-(4-cyanophenyl)-2,3-dihydro-5H-imidazo[4,5-f]benzoxazol-2-one
6-(1,2,5-thiadiazolyl)-2,3-dihydro-5H-imidazo[4,5-f]benzoxazol-2-one
6-(1,3,4-thiadiazolyl)-2,3-dihydro-5H-imidazo[4,5-f]benzoxazol-2-one
6-ethyl-2,3-dihydro-5H-imidazo[4,5-f]benzoxazol-2-one
6-butyl-2,3-dihydro-5H-imidazo[4,5-f]benzoxazol-2-one
6-hexyl-2,3-dihydro-5H-imidazo[4,5-f]benzoxazol-2-one
6-(2-propyl)-2,3-dihydro-5H-imidazo[4,5-f]-benzoxazol-2-one
6-(2-propenyl)-2,3-dihydro-5H-imidazo[4,5-f]benzoxazol-2-one
6-cyclopropyl-2,3-dihydro-5H-imidazo[4,5-f]benzoxazol-2-one
6-cyclohexyl-2,3-dihydro-5H-imidazo[4,5-f]benzoxazol-2-one
6-cyclopentyl-2,3-dihydro-5H-imidazo[4,5-f]benzoxazol-2-one
6-mercapto-2,3-dihydro-5H-imidazo[4,5-f]benzoxazol-2-one
6-methylthio-2,3-dihydro-5H-imidazo[4,5-f]benzoxazol-2-one
6-amino-2,3-dihydro-5H-imidazo[4,5-f]benzoxazol-2-one
6-(4-pyridylcarbonylamino)-2,3-dihydro-5H-imidazo[4,5-f]benzoxazol-2-one
6-(2-carboxyethyl)-2,3-dihydro-5H-imidazo[4,5-f]benzoxazol-2-one
6-(2-ethoxycarbonylethyl)-2,3-dihydro-5H-imidazo[4,5-f]benzoxazol-2-one
6-methoxymethyl-2,3-dihydro-5H-imidazo[4,5-f]benzoxazol-2-one
6-(4-pyridyl)-2,3-dihydro-5H-imidazo[4,5-f]benzoxazol-2-thione
6-(4-pyridyl)-2-methyl-5H-imidazo[4,5-f]benzoxazole
6-(4-pyridyl)-5H-imidazo[4,5-f]benzthiazole
6-(4-pyridyl)-2,3-dihydro-5H-imidazo[4,5-f]benzthiazol-2-thione
6-(3-pyridyl)-2-methyl-5H-imidazo[4,5-f]benzthiazole
6-(5-isoxazolyl)-1-methyl-1,2,3,5-tetrahydrobenzo[1,2-d:4,5-d']diimidazol-2-one
6-(5-isothiazolyl)-1-methyl-1,2,3,5-tetrahydrobenzo[1,2-d:4,5-d']diimidazol-2-one
6-(5-isoxazolyl)-2,3-dihydro-5H-imidazo[4,5-f]benzoxazol-2-one
6-(5-isothiazolyl)-2,3-dihydro-5H-imidazo[4,5-f]benzoxazol-2-one
6-(5-isoxazolyl)-2,3-dihydro-5H-imidazo[4,5-f]benzothiazol-2-one
6-(5-isothiazolyl)-2,3-dihydro-5H-imidazo[4,5-f]benzothiazol-2-one
6-(1,2,5-thiadiazol-3-yl)-2,3-dihydro-5H-imidazo[4,5-f]benzothiazol-2-one.

New compounds of general formulae (IX), (X) and (XI) are, apart from those mentioned in the Examples, the following:
6-nitro-5-(4-pyridylcarbonylamino)-benzoxazolinone
6-nitro-5-(3-pyridylcarbonylamino)-benzoxazolinone
6-nitro-5-(phenylcarbonylamino)-benzoxazolinone
6-nitro-5-(2-thienylcarbonylamino)-benzoxazolinone
6-nitro-5-(2-furylcarbonylamino)-benzoxazolinone
6-nitro-5-(4-pyridazinylcarbonylamino)-benzoxazolinone
5-nitro-6-(4-pyridylcarbonylamino)-benzoxazolinone
5-nitro-6-(3-pyridylcarbonylamino)-benzoxazolinone
5-nitro-6-(phenylcarbonylamino)-benzoxazolinone
5-nitro-6-(2-methoxyphenylcarbonylamino)-benzoxazolinone
5-nitro-6-(2-methylthiophenylcarbonylamino)-benzoxazolinone
5-nitro-6-(4-cyanophenylcarbonylamino)-benzoxazolinone
5-nitro-6-(2-furylcarbonylamino)-benzoxazolinone
5-nitro-6-(2-thienylcarbonylamino)-benzoxazolinone
5-nitro-6-(3-thienylcarbonylamino)-benzoxazolinone
5-nitro-6-(4-pyridazinylcarbonylamino)-benzoxazolinone
5-nitro-6-(5-pyrimidinylcarbonylamino)-benzoxazolinone
5-nitro-6-(5-pyrazinylcarbonylamino)-benzoxazolinone
5-nitro-6-(2-methyl-4-pyridinylcarbonylamino)-benzoxazolinone
5-nitro-6-(2-chloro-4-pyridinylcarbonylamino)-benzoxazolinone
7-bromo-2-methyl-6-(4-pyridylcarbonylamino)-benzoxazole
7-bromo-2-methyl-6-(3-pyridylcarbonylamino)-benzoxazole
7-bromo-2-methyl-6-(phenylcarbonylamino)-benzoxazole
7-bromo-2-methyl-6-(2-methoxyphenylcarbonylamino)-benzoxazole
7-bromo-2-methyl-6-(2-methylthiophenylcarbonylamino)-benzoxazole
7-bromo-2-methyl-6-(4-cyanophenylcarbonylamino)-benzoxazole
7-bromo-2-methyl-6-(3-pyridylcarbonylamino)-benzthiazole
7-bromo-2-methyl-6-(phenylcarbonylamino)-benzthiazole
7-bromo-2-methyl-6-(2-thienylcarbonylamino)-benzthiazole
7-bromo-2-methyl-6-(3-thienylcarbonylamino)-benzthiazole 7-bromo-2-methyl-6-(2-furylcarbonylamino)-benzthiazole 7-bromo-2-methyl-6-(4-pyridazinylcarbonylamino)-benzthiazole 7-bromo-2-methyl-6-(5-pyrimidinylcarbonylamino)-benzthiazole 7-bromo-2-methyl-6-(5-pyrazinylcarbonylamino)-benzthiazole 7-bromo-2-methyl-6-(2-methyl-4-pyridinylcarbonylamino)-benzthiazole 7-bromo-2-methyl-6-(2-methoxyphenylcarbonylamino)-benzthiazole 7-bromo-2-methyl-6-(2-methylthiophenylcarbonylamino)-benzthiazole 7-bromo-6-(4-pyridylcarbonylamino)-benzoxazole 7-bromo-6-(4-pyridylcarbonylamino)-benzthiazole.

The following Examples are given for the purpose of illustrating the present invention:

EXAMPLE 1

2-(4-Pyridyl)-1,5-dihydrobenzo[1,2-d:4,5-d']diimidazole 14.8 g. (100 mMole) 5,6-diaminobenzimidazole, 10.7 g. (100 mMole) pyridine-4-aldehyde and 5 ml. concentrated hydrochloric acid are heated to the boil under reflux. After the solution has been clarified with active charcoal, it is evaporated and the residue is digested with a little water. After suction filtration and drying, there are obtained 6.98 g. (29% of theory) of the desired product in the form of colourless crystals of the hydrochloride; m.p.>280° C.

EXAMPLE 2

6-(4-Pyridyl)-1-methyl-1,5-dihydrobenzo[1,2-d:4,5-d']diimidazole (a) 80 ml. 1M sodium methylate solution are added to a solution of 16.0 g. (76.9 mMole) 5,6-dinitrobenzimidazole in 500 ml. dimethylformamide and concentrated in a vacuum to about 150 ml. After the addition of 15 ml. (241 mMole) methyl iodide, the reaction mixture is stirred for 1 day at 40° C., whereafter the solution is poured into 1.5 liters of ice water. The precipitate obtained is filtered off with suction and dried to give 10 g. (58% of theory) 1-methyl-5,6-dinitrobenzimidazole in the form of colourless crystals; m.p. 238°–240° C.

(b) 4.40 g. (20.0 mMole) 1-methyl-5,6-dinitrobenzimidazole and 0.5 g. Adams catalyst in 250 ml. ethanol are hydrogenated for 4 hours at 40° C. and 4 bar hydrogen pressure. The catalyst is filtered off and the filtrate, after the addition of 2.10 g. (20.0 mMole) pyridine-4-aldehyde and 3 ml. concentrated hydrochloric acid, is heated to the boil under reflux. After chromatographed purification (silica gel; ethyl acetate/methanol 1:1 v/v) and evaporation of the appropriate fractions, there is obtained 1.1 g. (21% of theory) of the desired product in the form of colourless crystals of the semihydrochloride; m.p.>280° C.

EXAMPLE 3

In a manner analogous to that described in Example 2, there is obtained 6-(4-hydroxy-3,5-dimethoxyphenyl)-1-methyl-1,2,3,5-tetrahydrobenzo[1,2-d:4,5-d']diimidazole in the form of the hydrochloride; m.p.>280° C.

EXAMPLE 4

6-(3-Pyridyl)-1-methyl-1,2,3,5-tetrahydrobenzo[1,2-d:4,5-d']diimidazol-2-one (a) 2.20 g. (9.2 mMole) 5,6-dinitro-1-methylbenzimidazol-2-one is hydrogenated for 3 hours at 60° C. and 100 bar hydrogen pressure in 730 ml. methanol in the presence of 0.44 g. platinum oxide. The solution of 5,6-diamino-1-methyl-benzimidazol-2-one so obtained is, after filtration, used without further purification.

(b) 0.98 g. (9.2 mMole) pyridine-3-aldehyde and 73 mg. p-toluenesulphonic acid are mixed and added to the solution obtained under (a) above. The reaction mixture is heated under reflux for 2 hours, the solvent is removed in a vacuum and the residue is taken up in water and neutralised with 2N aqueous ammonia solution. The precipitate obtained is filtered off with suction and crystallized from isopropanol. There are obtained 450 mg. (20% of theory) of the desired product; m.p.>300° C.

With solutions of 5,6-diamino-1-methylbenzimidazol-2-one obtained analogously to Example 4(a) and the appropriate aldehydes, in the presence of catalytic amounts of the stated acids, the following compounds are prepared in a manner analogous to that described in Example 4(b):

| designation | yield (%) | m.p. | purification |
|---|---|---|---|
| EX. 4.1 | | | |
| 6-(4-pyridyl)-1-methyl-1,2,3,5-tetrahydrobenzo-[1,2-d:4,5-d']diimidazol-2-one from pyridine-4-aldehyde in the presence of concentrated hydrochloric acid | 35 | >320° C. | column chromatographically (silica gel; CH$_2$Cl$_2$:CH$_3$OH = 19:1) |
| EX. 4.2 | | | |
| 6-phenyl-1-methyl-1,2,3,5-tetrahydrobenzo-[1,2-d:4,5-d']diimidazol-2-one from benzaldehyde in the presence p-toluenesulphonic acid | 11 | >300° C. | crystallisation from ispropanol |
| EX. 4.3 | | | |
| 6-(4-dimethylaminophenyl)-1-methyl-1,2,3,5-tetrahydrobenzo[1,2-d:4,5-d']-diimidazol-2-one from p-dimethylaminobenzaldehyde in the presence of p-toluenesulphonic acid | 20 | 238–241° C. | recrystallisation twice from methanol |
| EX. 4.4 | | | |
| 6-[4-(1-imidazolyl)-phenyl]-1-methyl-1,2,3,5-tetrahydrobenzo[1,2-d:4,5-d']-diimidazol-2-one from 4-(1-imidazolyl)-benzaldehyde in the presence of p-toluenesulphonic acid | 7 | 260° C. (decomp.) | crystallisation from ethyl acetate |
| EX. 4.5 | | | |
| 6-(4-diethylamino-2-methoxyphenyl)-1-methyl-1,2,3,5-tetrahydrobenzo[1,2-d:4,5-d']diimidazol-2-one from 4-diethylamino-2-methoxybenzaldehyde in the presence of p-toluenesulphonic acid | 36 | >300° C. | crystallisation from methanol/dichloromethane |
| EX. 4.6 | | | |
| 6-(4-pyridyl)-1-ethyl-1,2,3,5-tetrahydrobenzo- | 28 | 237–239° C. | crystallisation |

-continued

| designation | yield (%) | m.p. | purification |
|---|---|---|---|
| [1,2-d:4,5-d']diimidazol-2-one from 5,6-diamino-1-ethyl-benz-imidazol-2-one and pyridyl-4-aldehyde in the presence of p-toluenesulphonic acid | | | from ethyl acetate |

Furthermore, the following compounds are prepared analogously to Example 4:

| designation | yield (%) | m.p. | purification |
|---|---|---|---|
| EX. 4.7 6-(4-pyridyl)-1-(1-propyl)-1,2,3,5-tetrahydrobenzo-[1,2-d:4,5-d']diimidazol-2-one from 5,6-diamino-1-(1-propyl)-benzimidazol-2-one and pyridyl-4-aldehyde in the presence of p-toluene-sulphonic acid | 21 | 235–237° C. | crystallisation from ethyl acetate |
| EX. 4.8 6-(2-furyl)-2,3-dihydro-5H—imidazo[4,5-f]benzoxazol-2-one from 5,6-diamino-benzoxazolin-2-one and furfural in the presence of p-toluene-sulphonic acid | 30 | 282–285° C. | crystallisation from isopropanol |
| EX. 4.9 6-(2-thienyl)-2,3-dihydro-5H—imidazo[4,5-f]benzoxazol-2-one from 5,6-diamino-benzoxazolin-2-one and thiophene-2-aldehyde in the presence of acetic acid | 14 | 270–274° C. | column chromatography (silica gel; dichloromethane:methanol = 15:1 v/v) |
| EX. 4.10 6-(3-thienyl)-2,3-dihydro-5H—imidazo[4,5-f]benzoxazol-2-one from 5,6-diamino-benzoxazolin-2-one and thiophene-3-aldehyde in the presence of acetic acid | 21 | 295–300° C. | crystallisation from dioxan/water |
| EX. 4.11 6-(4-pyridyl)-2,3-dihydro-5H—imidazo[4,5-f]benzthiazol-2-one from 5,6-diaminobenzthiazolin-2-one and pyridyl-4-aldehyde in the presence of acetic acid | 36 | >300° C. | extract with methanol from a thimble, dissolve residue in 2 N NaOH, acidify with glacial acetic acid, filter off with suction |

EXAMPLE 5

6-(4-Pyridazinyl)-2,3-dihydro-5H-imidazo[4,5-f]benzoxazol-2-one (a) 3.35 g. (17.2 mMole) 6-amino-5-nitrobenzoxazolin-one are hydrogenated at normal pressure in 120 ml. methanol in the presence of 0.5 g. 10% palladium on charcoal. After 1 hour, the catalyst is filtered off and the filtrate is evaporated in a vacuum. The residue is further reacted without purification.

(b) A mixture of 0.5 g. 5,6-diaminobenzoxazolin-2-one obtained in (a) above and 0.41 g. pyridazine-4-carboxylic acid with 5.4 g. hot polyphosphoric acid is maintained for 1 hour in a bath preheated to 150° C. After cooling, the reaction mixture is dissolved in 30 ml. ice water and neutralised with an aqueous solution of ammonia and the precipitate obtained is washed with water to give 0.38 g. of crude product. This is suspended in water, an aqueous solution of potassium hydroxide is added to the clear solution, followed by treatment with active charcoal. After suction filtration, the filtrate is neutralised and the precipitate obtained is filtered off with suction and washed with water to give 0.22 g. of the desired product in the form of the monohydrate; m.p. 330° C.

The following compounds are obtained analogously to Example 5:

| designation | yield (%) | m.p. | purification |
|---|---|---|---|
| EX. 5.1 6-pyrazinyl-2,3-dihydro-5H—imidazo[4,5-f]benzoxazol-2-one from 5,6-diaminobenzoxazolin-2-one and pyrazine carboxylic acid | 35 | 335° C. | treat with active charcoal in pyridine |
| EX. 5.2 6-(4-aminocarbonylphenyl)-2,3-dihydro-5H—imidazo-[4,5-f]benzoxazol-2-one from 5,6-diaminobenzoxazolin-2-one and 4-cyanobenzoic acid | 30 | >330° C. | treat with active charcoal in ethanol |
| EX. 5.3 6-(2-methoxyphenyl)-2,3-dihydro-5H—imidazo[4,5-f]-benzoxazol-2-one from 5,6-diaminobenzoxazolin-2-one and 2-methoxybenzoic acid | 39 | 319–321° C. | silica gel column: $CH_2Cl_2$: methanolic $NH_3$ = 10:1 v/v |
| EX. 5.4 6-(2-chloro-3-pyridyl)-2,3-dihydro-5H—imidazo[4,5-f]-benzoxazol-2-one from 5,6-diaminobenzoxazolin-2-one and 2-chloronicotinic acid | 8 | 310° C. (decomp.) | silica gel column: elution agent: butanol/acetic acid 80:20 v/v; crystallisation from methanol/diethyl ether |
| EX. 5.5 6-(2-methylthiophenyl)-2,3-dihydro-5H—imidazo[4,5-f]-benzoxazol-2-one from 5,6-diaminobenzoxazolin-2-one and 2-methylthiobenzoic acid | 36 | 208–211° C. | silica gel column, elution agent: ethyl acetate |
| EX. 5.6 6-(4-pyridazinyl)-1-methyl-1,2,3,5-tetrahydrobenzo-[1,2-d:4,5-d']diimidazol-2-one from 5,6-diamino-1-methylbenz-imidazol-2-one (see Example 4) and pyridazine-4-carboxylic acid | 14 | >300° C. | crystallisation from methanol/dichloromethane |
| EX. 5.7 6-(4-pyridazinyl)-1-ethyl-1,2,3,5-tetrahydrobenzo-[1,2-d:4,5-d']diimidazol-2-one from 5,6-diamino-1-ethyl-benz-imidazol-2-one and pyridazine-4-carboxylic acid | 14 | >300° C. | crystallisation from pyridine |
| EX. 5.8 6-(4-pyridylmethyl)-1-methyl- | 48 | >300° C. | |

| designation | yield (%) | m.p. | purification |
|---|---|---|---|
| 1,2,3,5-tetrahydrobenzo-[1,2-d:4,5-d']diimidazol-2-one from 5,6-diamino-1-methyl-benz-imidazol-2-one and 4-pyridylacetic acid | | | crystallisation from methanol |

EXAMPLE 6

6-Phenyl-2,3-dihydro-5H-imidazo[4,5-f]benzoxazol-2-one 1 g. Crude 5,6-diaminobenzoxazolin-2-one (obtained by hydrogenation of 6-amino-5-nitrobenzoxazolinone analogously to Example 5(a)) is suspended in 30 ml. methylene chloride and 1.82 g. triethylamine and 1.26 g. benzoyl chloride rapidly added dropwise thereto while cooling with ice. The resultant solution is stirred for 15 minutes at 10° C., a further 0.91 g. triethylamine and then a further 0.5 ml. benzoyl chloride are added dropwise thereto at 0° C. and the reaction mixture then stirred for 30 minutes at 10° C. and for 15 minutes at ambient temperature, evaporated in a vacuum and the evaporation residue triturated with about 30 ml. ice water to give 2.2 g. of solid crude product which is used in the following reaction step without further purification.

1.9 g. of this crude product is boiled under reflux for 5 hours with 82 ml. ethanol and 11 ml. concentrated hydrochloric acid, a further 11 ml. concentrated hydrochloric acid are added thereto, boiling under reflux is continued for 4 hours, the crystallisate obtained after cooling overnight is filtered off with suction and washed with ethanol and diethyl ether to give 0.62 g. of the desired compound in the form of the hydrochloride; m.p. about 350° C. (decomp.).

0.1 g. of this hydrochloride, after neutralisation with aqueous ammonia in aqueous suspension (to about pH 9), gives 0.08 g. of the desired product in the form of the free base containing 1 mole of water per mole; m.p. 298°–300° C.

The following compounds are obtained analogously to Example 6:

| designation | yield (%) | m.p. | purification |
|---|---|---|---|
| EX. 6.1 6-(4-pyridyl)-2,3-dihydro-5H—imidazo[4,5-f]benzoxazol-2-one from 5,6-diaminobenzoxazolin-2-one and 4-pyridincarbonyl chloride HCl | 51 | >360° C. | crystallisation from dimethylformamide |
| EX. 6.2 6-(3-pyridyl)-2,3-dihydro-5H—imidazo[4,5-f]benzoxazol-2-one from 5,6-diamino-benzoxazolin-2-one and 3-pyridincarbonyl chloride HCl | 28 | >360 | crystallisation from water/methanol |
| EX. 6.3 6-(2-methyl-4-pyridyl)-2,3-dihydro-5H—imidazo[4,5-f]-benzoxazol-2-one from 5,6-diamino-benzoxazolin-2-one and 2-methyl-4-pyridine-carbonyl chloride HCl | 11 | >300° C. (decomp.) | silica gel column, elution agent: butanol, acetic acid, water |
| EX. 6.4 6-(1-propyl)-2,3-dihydro-5H—imidazo[4,5-f]benzoxazol-2-one from 5,6-diamino-benzoxazolin-2-one and n-butyric acid anhydride | 34 | 177–180° C. | crystallisation from ethyl acetate |
| EX. 6.5 6-trifluoromethyl-2,3-dihydro-5H—imidazo[4,5-f]-benzoxazol-2-one from 5,6-diamino-benzoxazolin-2-one and trifluoroacetic acid anhydride | 45 | 348–350° C. | crystallisation from water |

EXAMPLE 7

6-Methyl-2,3-dihydro-5H-imidazo[4,5-f]benzoxazol-2-one (a) 4.9 g. 6-Aminobenzoxazolin-2-one (m.p. 190°–192° C.) are suspended in 112 ml. acetic anhydride and stirred for 3 hours at ambient temperature and then poured into 150 ml. ice water, stirred for 30 minutes, filtered off with suction and washed with water to give 5.7 g. 6-acetamido-benzoxazolin-2-one; m.p. 330°–332° C. (foaming).

(b) 2.85 g. of this benzoxazolinone derivative are introduced portionwise into 17 ml. concentrated sulphuric acid and stirred for about 1.5 hours until dissolved. A solution of 0.65 ml. nitric acid (d=1.51) in 5 ml. concentrated sulphuric acid of 0° C. is added dropwise thereto at −10° C., stirring is continued for 5 minutes at −10° C. and the reaction mixture is then poured into 100 ml. water+ice. After 30 minutes, the undissolved substance is filtered off with suction and washed with water to give 30 g. 6-acetamido-5-nitrobenzoxazolin-2-one; m.p. 213° C. After recrystallisation from 300 ml. methanol, the melting point is 244°–246° C. and the yield thus obtained is 2.7 g.

(c) 0.95 g. of this nitro compound is dissolved in 280 ml. warm methanol and hydrogenated for 1 hour at ambient temperature in the presence of 0.32 g. 10% palladium-charcoal catalyst. It is then filtered with suction, washed with methanol and the filtrate evaporated in a vacuum to give 0.7 g. 6-acetamido-5-aminobenzoxazolin-2-one; m.p.>320° C.

This 0.7 g. of acetamido compound is suspended in 14 ml. glacial acetic acid, the reaction mixture is introduced into a bath with a temperature of 100° C., maintained at this temperature for 1 hour and then evaporated in a vacuum. The evaporation residue is dissolved in 40 ml. water at about 50° C., treated with charcoal, neutralised with ammonia to about pH 8, left to stand for 20 minutes, filtered off with suction and washed with water to give 0.45 g. of the desired compound; m.p. 355° C. (decomp.).

In a manner analogous to that described in Example 7, from 5-acetylamino-6-nitro-1-methylbenzimidazol-2-one, there is obtained a yield of 66% of theory of 1,6-dimethyl-1,2,3,5-tetrahydrobenzo[1,2-d:4,5-d']diimidazol-2-one which, after crystallisation from isopropanol, has a melting point of 300° C.

EXAMPLE 8

2-Methyl-6-(4-pyridyl)-5H-imidazo[4,5-f]benzthiazole (a) 13.2 g. (80.0 mMole) 6-amino-2-methylbenzthiazole and 22.2 ml. (160 mMole) triethylamine are dissolved in 120 ml. dichloromethane. 14.3 g. (80.0 mMole) 4-pyridinecarbonyl chloride hydrochloride are added thereto with ice cooling. The solvent is removed in a vacuum and the residue is digested with water. After crystallisation from ethanol, there are obtained 17.0 g. (79% of theory) of colourless crystals of 2-methyl-6-(4-pyridylcarbonylamino)-benzthiazole; m.p. 209°–210° C.

(b) 15.9 g. (59.0 mMole) of the benzthiazole derivative obtained in (a) are dissolved in 60 ml. glacial acetic acid. After the addition of 5 ml. water, 3.4 ml. (65.0 mMole) bromine are added drop-wise thereto. 18.4 g. (59.0 mMole) silver sulphate are added thereto, followed by stirring for 2 hours at ambient temperature. The silver sulphate is filtered off and washed with a little glacial acetic acid. The filtrate is neutralised with ammonia and the precipitate obtained is filtered off with suction. After crystallisation from ethanol, there are obtained 12.5 g. (61%) of theory of colourless crystals of 7-bromo-2-methyl-6-(4-pyridylcarbonylamino)-benzthiazole; m.p. 194°–196° C.

(c) 12.5 g. (36.0 mMole) of the benzothiazole derivative obtained in (b) are introduced, with stirring, into a mixture of 1.7 ml. (40.0 mMole) fuming nitric acid and 30 ml. concentrated sulphuric acid cooled to −10° C. After stirring for 8 hours at ambient temperature, the solution is poured into ice water and the precipitate is filtered off with suction. After crystallisation from ethanol, there are obtained 7.3 g. (52% of theory) of crystalline 7-bromo-2-methyl-5-nitro-6-(4-pyridylcarbonylamino)-benzthiazole; m.p. 251°–253° C.

(d) 5.0 g. (12.7 mMole) of the nitro compound obtained according to (c) and 2.1 ml. (15.2 mMole) triethylamine are dissolved in 200 ml. methanol and then hydrogenated at normal pressure and ambient temperature in the presence of 1.0 g. palladium on charcoal. After filtering off the catalyst and removing the solvent in a vacuum, the residue is mixed with 4 ml. concentrated hydrochloric acid and stirred for 3 hours at 60° C. The solution is neutralised with 2N aqueous sodium hydroxide solution and the precipitate is filtered off with suction and purified over a short column of silica gel. After crystallisation from isopropanol, there are obtained 2.55 g. (75% of theory) of the desired compound; m.p.>300° C.

EXAMPLE 9

6-(4-Pyridyl)-1,2,3,5-tetrahyro[1,2-d:4,5-d']diimidazol-2-one (a) 10.0 g. (59.0 mMole) nitro-2,4,5-triaminobenzene and 20 ml. triethylamine are dissolved in 500 ml. dichloromethane and mixed portionwise with 11.6 g. (65.0 mMole) pyridine-4-carbonyl chloride hydrochloride. After stirring for 5 hours at ambient temperature, the solvent is removed in a vacuum and the residue is digested with water. The residue is boiled under reflux in 500 ml. ethanol and 80 ml. concentrated hydrochloric acid for 36 hours. The solvent is removed in a vacuum and the residue is digested with aqueous ammonia and filtered off with suction. There are obtained 12.0 g. (80% of theory) 5-amino-6-nitro-2-(4-pyridyl)-benzimidazole which is further used without further purification.

(b) 5 g. of the benzimidazole compound obtained according to (a) is hydrogenated at normal pressure and ambient temperature in 300 ml. methanol in the presence of 0.4 g. 10% palladium on charcoal. The catalyst is filtered off with suction, the filtrate is evaporated to dryness in a vacuum and the residue of 3 g. of 5,6-diamino-2-(4-pyridyl)-benzimidazole is used without further purification.

(c) 3.00 g. (13.3 mMole) of the benzimidazole compound obtained according to (b) are dissolved in 120 ml. 2N hydrochloric acid and phosgene passed through the solution. The precipitate obtained is digested with an aqueous solution of ammonia and filtered off with suction. After crystallisation from methanol/dichloromethane (4:1 v/v) there is obtained 0.72 g. (22% of theory) of the desired compound; m.p. >300° C.

In a manner analogous to that described in Example 9 (c), from 3.5 g. 5,6-diamino-1-methylbenzimidazolin-2-one in 70 ml. 2N hydrochloric acid, after passing through phosgene for 4 hours and leaving to stand overnight, there is obtained 1-methyl-1,2,3,5,6,7-hexahydro[1,2-d:4,5-d']diimidazole-2,6-dione; m.p. >300° C.

EXAMPLE 10

2,3,5,6-Tetrahydro-7H-imidazo[4,5-f]benzoxazol-2,6-dione 3.3 g. (0.02 mole) 5,6-diaminobenzoxazolin-2-one and 5.5 g. (0.034 mole) 1,1'-carbonyldiimidazole are dissolved in 150 ml. dioxan and heated to the boil for 3 hours. After cooling to ambient temperature, the brownish crystalline substance obtained is filtered off with suction, boiled with dimethylformamide, filtered with suction and washed with methanol. There is obtained a yield of 65% of theory of the desired compound; m.p. >360° C.

EXAMPLE 11

6-(N-Oxy-4-pyridyl)-1,2-dihydro-5H-imidazo[4,5-f]benzoxazol-2-one 1.9 g. (7.5 mMole) 6-(4-pyridyl)-1,2-dihydro-5H-imidazo[4,5-f]benzoxazol-2-one is suspended in 20 ml. glacial acetic acid and 6 ml. 30% hydrogen peroxide are added thereto. After 3 weeks, the suspension is stirred into water and the precipitate filtered off with suction. Purification is carried out by column chromatography on silica gel with a butanol-acetic acid-water mixture. The appropriate fractions are evaporated in a vacuum, the residue is dissolved in 2N aqueous sodium hydroxide solution, undissolved material is filtered off and the solution is acidified with hydrochloric acid. The precipitate obtained is filtered off with suction, washed with water and dried at 120° C. There is obtained 0.6 g. (30% of theory) of the desired compound; m.p. >360° C.

EXAMPLE 12

2-Amino-6-(4-pyridyl)-1,5-dihydrobenzo[1,2-d:4,5-d']diimidazole 2.9 g. 5,6-diamino-2-(4-pyridyl)-benzimidazole and 1.3 g. cyanogen bromide are stirred for 2 hours at 85° C. with the exclusion of moisture. After cooling to ambient temperature, the reaction mixture is treated with active charcoal, filtered and the filtrate evaporated to dryness. The residue is suspended in water, the pH value is adjusted to 8.5 with aqueous ammonia solution and filtered off with suction. The 1.47 g. of residue obtained is applied to 15 g. silica gel 60 and eluted with a mixture of methylene chloride and ammoniacal methanol (95:5 v/v to 92:8 v/v). The appropriate fractions are evaporated to dryness and the residue is dissolved in methanol. Isopropanol is added thereto until turbid and then left to crystallise. There is obtained 0.52 g. of the desired compound; m.p. >320° C.

EXAMPLE 13

2-Acetylamino-6-(4-pyridyl)-1,5-dihydrobenzo[1,2-d:4,5-d']diimidazole 210 mg. of the compound obtained according to Example 12 are stirred for 4 days at 50° C. in 20 ml. acetic anhydride. The reaction mixture is mixed with 7 mg. sodium acetate and, after 2 hours, is distilled to dryness in a high vacuum. The 160 mg. of residue are purified by column chromatography (silica gel; methylene chloride/ammoniacal methanol; 98:2 v/v to 92:8 v/v). The appropriate fractions are combined and distilled to dryness and the residue is crystallised from methanol. There are obtained 105 mg. of the desired compound; m.p. >330° C.

Pharmaceutical Activity

The following experiment demonstrates the pharmaceutical activity of compound (I) of the invention:

Male Sprague-Dawley rats weighing between 350 and 450 g were narcotized by intraperitoneal injection of a barbiturate and fitted with instrumentation for the examinations as follows:

A pressure measuring catheter (Millar Mikrotip TM-/diameter 0.5 mm) was inserted through the arteria carotis dextra into the left ventricle. The pressure inside the left ventricle was continually registered through this catheter. The signal from this mikrotip was electronically differentiated and $(dp/dt)_{60}$—the slope of the pressure-time curve at a pressure of 60 mm Hg—was taken as a measure for the inotropy.

A polypropylene catheter was bound in a vena jugularis for the intravenous injection of the test substances.

A further polypropylene catheter was inserted through an arteria femoralis into the abdominal aorta for the direct measurement of the arterial blood pressure.

The ECG was traced with subcutaneous insertion electrodes.

During the preparation of the animal and during the entire test period the rats were fixed on a electrically heated and thermostated operating table.

The test substances were always introduced by intravenous injection, with an injection volume, per injection, of 1 ml/kg body weight. In intervals of 10 min. each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criteria for the effectiveness of the substances, the maximum effect obtained maximal increase of $(dp/dt)_{60}$ and its corresponding dose were determined. Table (I) below shows the equipotent doses ($DE_{1.5}$=the dose in mg/kg that leads to an increase of $(dp/dt)_{60}$ of 1.5 mHg/sec) and the maximal effectiveness ($W_{max}$=the maximal increase of $(dp/dt)_{60}$.

TABLE (I)

| Compound | $DE_{1.5}$ mHg/sec [mg/kg i.v.] | $W_{max}$ [mHg/sec] | [mg/kg i.v.] |
|---|---|---|---|
| Ex. 4    | 0,29 | 3,1 | 3,0  |
| Ex. 4.1  | 0,33 | 2,6 | 10,0 |
| Ex. 4.6  | 0,05 | 2,3 | 3,0  |
| Ex. 5.6  | 0,19 | 2,8 | 1,0  |
| Ex. 5.7  | 0,04 | 3,2 | 3,0  |
| Ex. 6.1  | 0,52 | 4,1 | 10,0 |
| Ref. 1   | 1,17 | 3,5 | 10,0 |
| Ref. 2   | 3,0  | 0,6 | 3,0  |

The corresponding dose is shown in brackets.

Ref. 1: 3-Amino-6-methyl-5-phenyl-2-(1H)-pyridinone-methane-sulfonate (from British Patent Application No. GB 2,070,606).

Ref. 2: 3,4-Dihydro-6-[4-(3,4-dimethoxybenzoyl)-1-piperazinyl]-2(1H)-quinolinone (from U.S. Pat. No. 4,415,572).

It will be understood that the specification and examples are illustrative but not limitative of the present invention and that other embodiments within the spirit and scope of the invention will suggest themselves to those skilled in the art.

What is claimed is:

1. A benzimidazole of the formula:

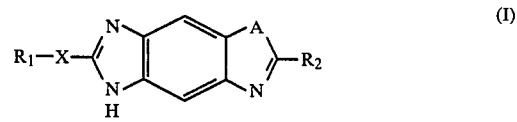

wherein

X is a valency bond, a $C_1$–$C_4$-alkylene radical or a vinylene radical;

$R_1$ is an aromatic heterocyclic five-membered or six-membered ring selected from the group consisting of pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridyl and N-oxypyridyl, said five- and six-membered rings being unsubstituted or substituted one or more times by $C_1$–$C_6$ alkyl, $C_1$–$C_6$ alkoxy, $C_1$–$C_6$ alkylthio, hydroxyl, nitro, amino, halogen or cyano, or $R_1$ is a phenyl radical of the formula:

wherein $R_3$, $R_4$ and $R_5$, which can be the same or different, are hydrogen or $C_1$–$C_5$ alkanesulphonyloxy, trifluoromethanesulphonyloxy, $C_1$–$C_5$ alkanesulphonylamino, trifluoromethanesulphonylamino, N—$C_1$–$C_5$ alkyl-$C_1$–$C_5$ alkanesulphonylamino, N—$C_1$–$C_5$ alkyl-trifluoromethanesulphonylamino, $C_1$–$C_5$ alkylsulphenylmethyl, $C_1$–$C_5$-alkyl-sulphinylmethyl or $C_1$–$C_5$ alkyl-sulphonylmethyl, or are carbonyl groups substituted by a hydroxyl, $C_1$–$C_5$ alkoxy, amino, hydrazino, $C_1$–$C_5$ alkylamino, di-$C_1$–$C_5$ alkylamino or cyclic imino selected from the group consisting of morpholino-, pyrrolidino-, piperidino- and hexamethylene imino or are sulphonyl groups substituted by an amino, $C_1$–$C_5$ alkylamino, di-$C_1$–$C_5$ alkyl-amino or cyclic imino selected from the group consisting of morpholino-, pyrrolidino-, piperidino- and hexamethylene imino, or are $C_1$–$C_5$ alkyl-carbonylamino, N—$C_1$–$C_5$ alkyl-$C_1$–$C_5$ alkyl-carbonylamino, aminocarbonylamino, $C_1$–$C_5$ alkyl-amino-carbonylamino, di-$C_1$–$C_5$ alkylaminocarbonylamino or are $C_1$–$C_5$ alkythio, $C_1$–$C_5$ alkylsulphinyl, $C_1$–$C_5$ alkyl-sulphonyl or $C_1$–$C_5$ alkyloxysulphonyl, or are $C_2$–$C_5$ alkenyloxy, $C_2$–$C_5$ alkynyloxy, cyano-$C_1$–$C_5$ alkoxy, carboxy-$C_1$–$C_5$ alkoxy, $C_1$–$C_5$ alkoxy-carbonyl-$C_1$–$C_5$ alkoxy or are nitro, halogen, amino, mercapto, hydroxyl, $C_1$–$C_5$ alkyl, $C_1$–$C_5$ alkoxy, $C_1$–$C_5$ alkylamino, di-$C_1$–$C_5$ alkyl-amino, 1-imidazolyl, trifluoromethyl or cyano or, when X represents a valency bond, besides the above-mentioned groups, $R_1$ can also be hydrogen, $C_1$–$C_8$ alkyl, $C_2$–$C_8$ alkenyl, $C_2$–$C_8$ alkynyl, $C_3$–$C_7$ cycloalkyl, $C_5$ or $C_6$ cycloalkenyl, $C_1$–$C_8$ haloalkyl, trifluoromethyl, hydroxyl; mercapto, amino, $C_1$–$C_5$ alkylthio, pyridylcarbonylamino, carboxy-$C_1$–$C_5$-alkyl, $C_1$–$C_5$ alkoxy-carbonyl-$C_1$–$C_5$ alkyl or $C_1$–$C_5$ alkoxy-$C_1$–$C_5$ alkyl group;

A is an oxygen or sulphur atom or an N—$R_6$ group, wherein $R_6$ is hydrogen or $C_1$–$C_6$ alkyl and $R_2$ is hydrogen, hydroxyl, mercapto or amino or $C_1$–$C_6$ alkyl, $C_1$–$C_6$ alkylthio, $C_1$–$C_6$ alkyl-carbonylamino, N—$C_1$–$C_5$ alkyl-$C_1$–$C_6$ alkyl-carbonylamino, $C_1$–$C_6$ alkyl-aminocarbonylamino, di-$C_1$–$C_6$ alkyl-aminocarbonylamino, aminocarbonylamino or pyridylcarbonylamino; a tautomer thereof or a physiologically acceptable salt thereof with an inorganic or organic acid provided that when A is the group $NR_6$ wherein $R_6$ is hydrogen, and X is a valency bond, $R_1$ cannot be methyl, 4-aminophenyl or hydroxy and $R_2$ cannot be methyl, hydrogen or hydroxy.

2. The benzimidazole of claim 1, wherein $R_1$ is a pyrrole, furan, thiophene, pyrazole, imidazole, thiazole, isothiazole, oxazole, isoxazole, triazole, tetrazole, thiadiazole, oxadiazole, pyridine, N-oxypyridine, pyrazine, N,N-dioxypyrazine, pyrimidine, N,N-dioxypyrimidine, pyridazine, oxazine, thiazine, triazine or tetrazine radical or a methyl, ethyl, methoxy, ethoxy, methylthio, ethylthio or chloro-substituted derivative thereof or is a phenyl radical of formula (II), wherein $R_3$ is a hydrogen atom or a methanesulphonyloxy, trifluoromethanesulphonyloxy, methanesulphonylamino, trifluoromethanesulphonylamino, methanesulphonylmethylamino, trifluoromethanesulphonylmethylamino, methylsulphenylmethyl, methylsulphinylmethyl, methylsulphonylmethyl, aminocarbonyl, aminosulphonyl, methylaminosulphonyl, dimethylaminosulphonyl, acetylamino, methylthio, methylsulphonyl, hydroxyl, methyl, methoxy, propargyloxy, cyanomethoxy, methoxycarbonylmethoxy, cyano, chloro, nitro, amino, dimethylamino, trifluoromethyl or 1-imidazolyl radical, $R_4$ is a hydrogen or chlorine atom or a methyl, methoxy or dimethylamino radical and $R_5$ is a hydrogen atom or a methoxy radical or, when X is a valency bond, besides the above-mentioned groups, $R_1$ can also be a hydrogen atom or a methyl, ethyl, propyl, isopropyl, butyl, 2-butyl, tert.-butyl, pentyl, hexyl, prop-2-enyl, prop-1-enyl, prop-1-ynyl, cyclopropyl, cyclobutyl, cyclopentyl, cyclopent-1-enyl, methoxymethyl, ethoxycarbonylethyl, carboxyethyl, hydroxy, mercapto, methylthio, amino, pyridylcarbonylamino or trifluoromethyl radical, X is a valency bond, an alkylene radical containing 1 or 2 carbon atoms or a vinylene radical, A is an oxygen or sulphur atom or an N—$R_6$ group, in which $R_6$ is a hydrogen atom or a methyl, ethyl, propyl or isopropyl radical and $R_2$ is a hydrogen atom or a methyl, ethyl, propyl, isopropyl, butyl, 2-butyl, tert.-butyl, hydroxyl, amino, mercapto, methylthio, methylcarbonylamino, pyridylcarbonylamino, methylaminocarbonylamino or aminocarbonylamino radical; a tautomer thereof or a physiologically acceptable salt thereof with an inorganic or organic acid.

3. The benzimidazole of claim 1 or 2, wherein $R_1$ is a pyridine, N-oxypyridine, pyridazine, pyrimidine, pyrazine, furan or thiophene radical which is unsubstituted or substituted by alkyl and/or halogen, a phenyl radical which is unsubstituted or substituted once or twice by methoxy, methylthio, aminocarbonyl, dimethylamino, diethylamino, 1-imidazolyl and/or hydroxyl, or is a methyl, trifluoromethyl, n-propyl or hydroxyl radical, X is a valency bond or a methylene or vinylene radical, A is an oxygen or sulphur atom or an N—$R_6$ group, in which $R_6$ is a hydrogen atom or a methyl, ethyl or n-propyl radical, and $R_2$ is a hydrogen atom or a hydroxyl, methyl, amino or acetamido radical; a tautomer thereof or a physiologically acceptable salt thereof with an inorganic or organic acid.

4. The benzimidazole of claim 1 wherein X is a valency bond or methylene.

5. The benzimidazole of claim 1 wherein A is oxygen.

6. The benzimidazole of claim 1 wherein A is sulphur.

7. The benzimidazole of claim 1 wherein A is the N—$R_6$ group.

8. The benzimidazole of claim 1 wherein X is a valency bond, and $R_1$ is pyridine or pyridazine.

9. The benzimidazole of claim 1 wherein $R_2$ is hydroxyl.

10. The benzimidazole of claim 1 designated 6-(3-pyridyl)-1-methyl-1,2,3,5-tetrahydrobenzo[1,2-d:4,5-d']diimidazol-2-one.

11. The benzimidazole of claim 1 designated 6-(4-pyridyl)-1-methyl-1,2,3,5-tetrahydrobenzo[1,2-d:4,5-d']diimidazol-2-one.

12. The benzimidazole of claim 1 designated 6-(4-pyridyl)-1-ethyl-1,2,3,5-tetrahydrobenzo[1,2-d:4,5-d']diimidazol-2-one.

13. The benzimidazole of claim 1 designated 6-(4-pyridazinyl)-1-methyl-1,2,3,5-tetrahydrobenzo[1,2-d:4,5-d']diimidazol-2-one.

14. The benzimidazole of claim 1 designated 6-(4-pyridazinyl)-1-ethyl-1,2,3,5-tetrahydrobenzo[1,2-d:4,5-d']diimidazol-2-one.

15. The benzimidazole of claim 1 designated 6-(4-pyridyl)-2,3-dihydro-5H-imidazo[4,5-f]benzoxazol-2-one.

16. A pharmaceutical composition for the prophylaxis or treatment of heart or circulatory diseases which respond to a lowering of blood pressure, a positive inotropic action and/or an improvement in microcirculation and containing an effective amount of at least one benzimidazole of claim 1.

17. The pharmaceutical composition of claim 16 wherein the benzimidazole is
6-(3-pyridyl)-1-methyl-1,2,3,5-tetrahydrobenzo[1,2-d:4,5-d']diimidazol-2-one, 6-(4-pyridyl)-1-methyl-1,2,3,5-tetrahydrobenzo[1,2-d:4,5-d']diimidazol-2-one, 6-(4-pyridyl)-1-ethyl-1,2,3,5-tetrahydrobenzo[1,2-d:4,5-d']diimidazol-2-one, 6-(4-pyridazinyl)-1-methyl-1,2,3,5-tetrahydrobenzo[1,2-d:4,5-d']diimidazol-2-one, 6-(4-pyridazinyl)-1-ethyl-1,2,3,5-tetrahydrobenzo[1,2-d:4,5-d']diimidazol-2-one, or 6-(4-pyridyl)-2,3-dihydro-5H-imidazo[4,5-f]benzoxazol-2-one.

18. A pharmaceutical composition for the prophylaxis or treatment of heart or circulatory diseases which respond to a lowering of blood pressure, a positive inotropic action and/or an improvement in microcirculation and containing an effective amount of at least one benzimidazole of the formula:

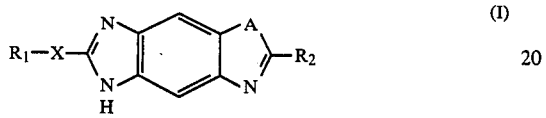

wherein

X is a valency bond, a $C_1$-$C_4$-alkylene radical or a vinylene radical;

$R_1$ is an aromatic heterocyclic five-membered or six-membered ring selected from the group consisting of pyrrole, furan, thiophene, pyrazole, imidazole, thiazole, isothiazole, oxazole, isoxazole, triazole, tetrazole, thiadiazole, oxadiazole, pyrazine, N,N-dioxypyrazine, pyrimidine, N,N-dioxypyrimidine, pyridazine, oxazine, thiazine, triazine, tetrazine, pyridyl and N-oxypyridyl, said five- and six-membered rings being unsubstituted or substituted one or more times by $C_1$-$C_6$ alkyl, $C_1$-$C_6$ alkoxy, $C_1$-$C_6$ alkylthio, hydroxyl, nitro, amino, halogen or cyano, or $R_1$ is a phenyl radical of the formula:

wherein $R_3$, $R_4$ and $R_5$, which can be the same or different, are hydrogen or $C_1$-$C_5$ alkanesulphonyloxy, trifluoromethanesulphonyloxy, $C_1$-$C_5$ alkanesulphonylamino, trifluoromethane sulphonylamino, N—$C_1$-$C_5$ alkyl-$C_1$-$C_5$ alkanesulphonylamino, N—$C_1$-$C_5$ alkyl-trifluoromethanesulphonylamino, $C_1$-$C_5$ alkylsulphenylmethyl, $C_1$-$C_5$-alkyl-sulphinylmethyl or $C_1$-$C_5$ alkylsulphonylmethyl, or are carbonyl groups substituted by a hydroxyl, $C_1$-$C_5$ alkoxy, amino, hydrazino, $C_1$-$C_5$ alkylamino, di-$C_1$-$C_5$ alkyl-amino or cyclic imino selected from the group consisting of morpholino-, pyrrolidino-, piperidino- and hexamethylene imino or are sulphonyl groups substituted by an amino, $C_1$-$C_5$ alkylamino, di-$C_1$-$C_5$ alkyl-amino or cyclic imino selected from the group consisting of morpholino-, pyrrolidino-, piperidino- and hexamethylene imino, or are $C_1$-$C_5$ alkyl-carbonylamino, N—$C_1$-$C_5$ alkyl-$C_1$-$C_5$ alkyl-carbonylamino, aminocarbonylamino, $C_1$-$C_5$ alkyl-amino-carbonylamino, di-$C_1$-$C_5$ alkylaminocarbonylamino or are $C_1$-$C_5$ alkythio, $C_1$-$C_5$ alkylsulphinyl, $C_1$-$C_5$ alkyl-sulphonyl or $C_1$-$C_5$ alkyloxysulphonyl, or are $C_2$-$C_5$ alkenyloxy, $C_2$-$C_5$ alkynyloxy, cyano-$C_1$-$C_5$ alkoxy, carboxy-$C_1$-$C_5$ alkoxy, $C_1$-$C_5$ alkoxy-carbonyl-$C_1$-$C_5$ alkoxy or are nitro, halogen, amino, mercapto, hydroxyl, $C_1$-$C_5$ alkyl, $C_1$-$C_5$ alkoxy, $C_1$-$C_5$ alkylamino, di-$C_1$-$C_5$ alkyl-amino, 1-imidazolyl, trifluoromethyl or cyano or, when X represents a valency bond, besides the above-mentioned groups, $R_1$ can also be hydrogen, $C_1$-$C_8$ alkyl, $C_2$-$C_8$ alkenyl, $C_2$-$C_8$ alkynyl, $C_3$-$C_7$ cycloalkyl, $C_5$ or $C_6$ cycloalkenyl, $C_1$-$C_8$ haloalkyl, trifluoromethyl, hydroxyl; mercapto, amino, $C_1$-$C_5$ alkylthio, pyridylcarbonylamino, carboxy-$C_1$-$C_5$-alkyl, $C_1$-$C_5$ alkoxy-carbonyl-$C_1$-$C_5$ alkyl or $C_1$-$C_5$ alkoxy-$C_1$-$C_5$ alkyl group;

A is an oxygen or sulphur atom or an N—$R_6$ group, wherein $R_6$ is hydrogen or $C_1$-$C_6$ alkyl and $R_2$ is hydrogen, hydroxyl, mercapto or amino or $C_1$-$C_6$ alkyl, $C_1$-$C_6$ alkylthio, $C_1$-$C_6$ alkyl-carbonylamino, N—$C_1$-$C_5$ alkyl-$C_1$-$C_6$ alkyl-carbonylamino, $C_1$-$C_6$ alkyl-aminocarbonylamino, di-$C_1$-$C_6$ alkyl-aminocarbonylamino, aminocarbonylamino or pyridylcarbonylamino; a tautomer thereof or a physiologically acceptable salt thereof with an inorganic or organic acid in a pharmaceutical carrier.

19. A method of treating heart or circulatory diseases which respond to a lowering of blood pressure, a positive inotropic action and/or an improvement in microcirculation comprising administering an effective amount for treating said heart or circulatory diseases, of the pharmaceutical composition of claim 17.

20. A method of treating heart or circulatory diseases which respond to a lowering of blood pressure, a positive inotropic action and/or an improvement in microcirculation comprising administering an effective amount for treating said heart or circulatory diseases, of the benzimidazole of claim 1.

* * * * *

UNITED STATES PATENT AND TRADEMARK OFFICE
CERTIFICATE OF CORRECTION

PATENT NO. : 4,831,032

DATED : May 16, 1989

INVENTOR(S) : Wolfgang Von Der Saal, et al.

It is certified that error appears in the above-identified patent and that said Letters Patent is hereby corrected as shown below:

Col. 3, line 15 : delete "methyllsulphonyl" and insert -- methylsulphonyl --.

Col. 3, line 47 : delete "preerably" and insert -- preferably --.

Col. 8, entry (VIII) : delete "+ $R'_1-X-\overset{O}{\underset{\|}{C}}-X$" and insert -- + $R'_1-X-\overset{O}{\underset{\|}{C}}-Z$ --.

Signed and Sealed this

Seventeenth Day of July, 1990

Attest:

HARRY F. MANBECK, JR.

Attesting Officer

Commissioner of Patents and Trademarks